United States Patent
Lapotko et al.

(10) Patent No.: US 11,859,177 B2
(45) Date of Patent: Jan. 2, 2024

(54) THERANOSTIC METHODS AND SYSTEMS FOR DIAGNOSIS AND TREATMENT OF MALARIA

(71) Applicant: WILLIAM MARSH RICE UNIVERSITY, Houston, TX (US)

(72) Inventors: Dmitri Lapotko, Pearland, TX (US); Katsiaryna Hleb, Houston, TX (US); Janet Braam, Bellaire, TX (US); John S. Olson, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 16/523,398

(22) Filed: Jul. 26, 2019

(65) Prior Publication Data
US 2019/0345478 A1   Nov. 14, 2019

Related U.S. Application Data

(63) Continuation of application No. 14/333,145, filed on Jul. 16, 2014, now abandoned, which is a continuation of application No. PCT/US2013/021889, filed on Jan. 17, 2013.

(60) Provisional application No. 61/587,264, filed on Jan. 17, 2012.

(51) Int. Cl.
| | |
|---|---|
| *G01N 21/49* | (2006.01) |
| *G01N 21/63* | (2006.01) |
| *C12N 13/00* | (2006.01) |
| *A61B 5/00* | (2006.01) |
| *A61B 5/1455* | (2006.01) |
| *A61B 5/145* | (2006.01) |
| *A61N 5/06* | (2006.01) |

(Continued)

(52) U.S. Cl.
CPC ............ *C12N 13/00* (2013.01); *A61B 5/0095* (2013.01); *A61B 5/1455* (2013.01); *A61B 5/14546* (2013.01); *A61N 5/0624* (2013.01); *A61N 5/0625* (2013.01); *G01N 21/49* (2013.01); *G01N 21/636* (2013.01); *G01N 21/6458* (2013.01); *A61N 5/067* (2021.08); *A61N 2005/0627* (2013.01); *A61N 2005/0662* (2013.01); *G01N 2021/6439* (2013.01)

(58) Field of Classification Search
None
See application file for complete search history.

(56) References Cited

U.S. PATENT DOCUMENTS

| | | |
|---|---|---|
| 5,371,368 A | 12/1994 | Alfano et al. |
| 5,872,627 A | 2/1999 | Miers |
| 2009/0318784 A1 | 12/2009 | Newman et al. |

(Continued)

OTHER PUBLICATIONS

Newman et al., The In Vivo Diagnosis of Malaria: Feasibility Study Into a Magneto-Optic Fingertip Probe, May/Jun. 2010, vol. 16, pp. 573-580, IEEE Journal of Selected Topics in Quantum Electronics (Year: 2010).*

(Continued)

*Primary Examiner* — Neil N Turk
(74) *Attorney, Agent, or Firm* — Reed Smith LLP; Robert R. Riddle; Hallie H. Wimberly

(57) ABSTRACT

Methods, systems, and apparatuses for employing nanobubbles for theranostic purposes are provided. In one embodiment, a method comprising introducing a photothermal nanobubble into a malaria-infected red blood cell is provided.

6 Claims, 12 Drawing Sheets

(51) Int. Cl.
    *G01N 21/64*     (2006.01)
    *A61N 5/067*     (2006.01)

(56) References Cited

U.S. PATENT DOCUMENTS

| | | |
|---|---|---|
| 2010/0222774 A1 | 9/2010 | Hegg et al. |
| 2011/0204257 A1 | 8/2011 | Wiseman et al. |
| 2011/0222059 A1* | 9/2011 | Behrend ............... G01N 21/00 356/317 |

OTHER PUBLICATIONS

Wilson et al., Detection of malarial byproduct hemozoin utilizing its unique scattering properties, Jun. 2011, vol. 19, No. 13, Optics Express (Year: 2011).*

Apotko, D. "Plasmonic Nanoparticle-Generated Photothermal Bubbles and Their Biomedical Applications." Nanomedicine. 2009. vol. 4, No. 7, pp. 813-845. DOI 10.1002/LSM.20284.

Lapotko, D. "Laser-Induced Bubbles in Living Cells." Lasers in Surgery and Medicine. Feb. 9, 2006. vol. 38, pp. 240-248. DOI 10.1002/ISM.20284.

Jul. 22, 2014, International Preliminary Report on Patentability for PCT/US13/21889.

May 24, 2013, Written Opinion of the International Searching Authority for PCT/US13/21889.

* cited by examiner a b c d e f

THERANOSTIC METHODS AND SYSTEMS FOR DIAGNOSIS AND TREATMENT OF MALARIA

CROSS-REFERENCE TO RELATED APPLICATIONS

This application is a continuation of U.S. patent application Ser. No. 14/333,145 filed Jul. 16, 2014 which is a continuation of PCT/US2013/21889 filed Jan. 17, 2013 and claims the benefit of U.S. Provisional Patent Application Ser. No. 61/587,264, filed Jan. 17, 2012, the entire disclosures of which are incorporated herein by reference.

STATEMENT OF GOVERNMENT INTEREST

This invention was made with government support under Grant Numbers R01GM35649, R01GM094816, and R01 HL047020 awarded by the National Institute of Health. The United States government has certain rights in this invention.

BACKGROUND

Malaria is a widespread and infectious disease that may cause serious illness and death in humans and occurs when a *Plasmodium* parasite infects the red blood cells of a host. The parasite digests hemoglobin found in the host's red blood cells and produces nanocrystals known as hemozoin. Hemozoin nanocrystals are present in all *Plasmodium* species and in all *Plasmodium* erythrocyte stages. While it is often possible to diagnose and treat malaria, current diagnostic and treatment methods for malaria are costly, often complicated, and may not achieve desired rates of effectiveness. In addition, drug resistance to known treatment methods is a growing concern. Early detection and innovative approaches for parasite destruction are needed.

DRAWINGS

Figure 1:
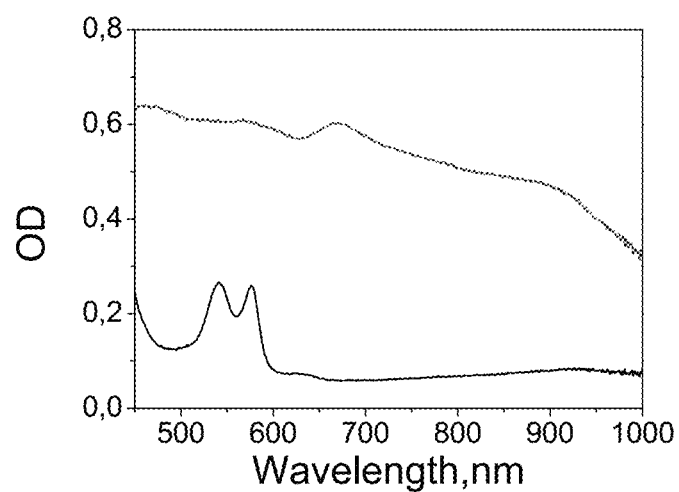

FIG. 1. Optical absorbance spectra of Hb (black) and Hz (red) suspensions of identical concentrations show that volume-averaged absorbance of Hemozoin (Hz) nanocrystal suspension (represented by Hz nanocrystals in PBS) significantly exceeds that of Hb solution.

Figure 2:
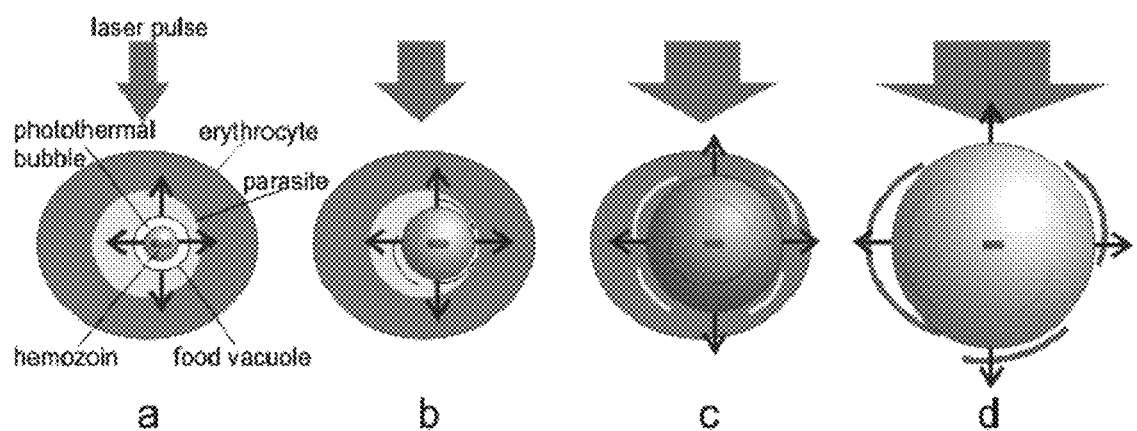

FIG. 2. Principle of therapeutic action of the laser-induced photothermal nanobubble (PTNB) generated around a nanocrystal of Hz upon exposure to a short laser pulse that is absorbed and converted by Hz into a localized transient thermal field that evaporates the liquid environment of the Hz crystal and thus generates PTNB with explosive, mechanical effect on surrounding targets. (a) Low energy pulse induces small PTNBs that destroys the Hz crystal. (b) Increased energy of the laser pulse induces larger PTNBs that destroys the food vacuole of malaria parasite. (c) Further increase of laser energy generates even larger PTNBs that destroys the whole parasite. (d) Even higher pulse energy produces PTNBs that destroys the malaria-infected red blood cell (MIRBC) with all its internal structures.

Figure 3:
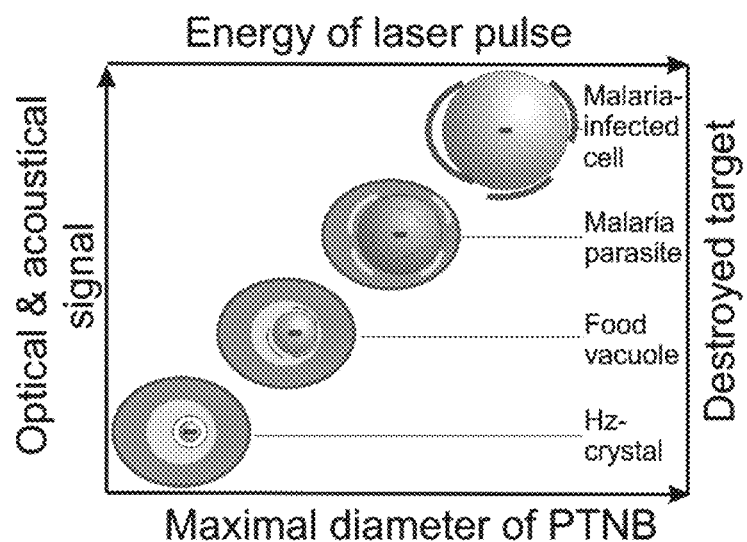

FIG. 3. Principle of malaria theranostics with PTNBs: maximal diameter of PTNBs is determined by laser energy; both PTNBs signals and the therapeutic effect of PTNBs (destroyed target) are determined by the maximal diameter of the PTNB; as a result optical and acoustical signals can be used to detect the malaria and to guide the therapeutic action of PTNBs in one theranostic procedure.

Figure 4:
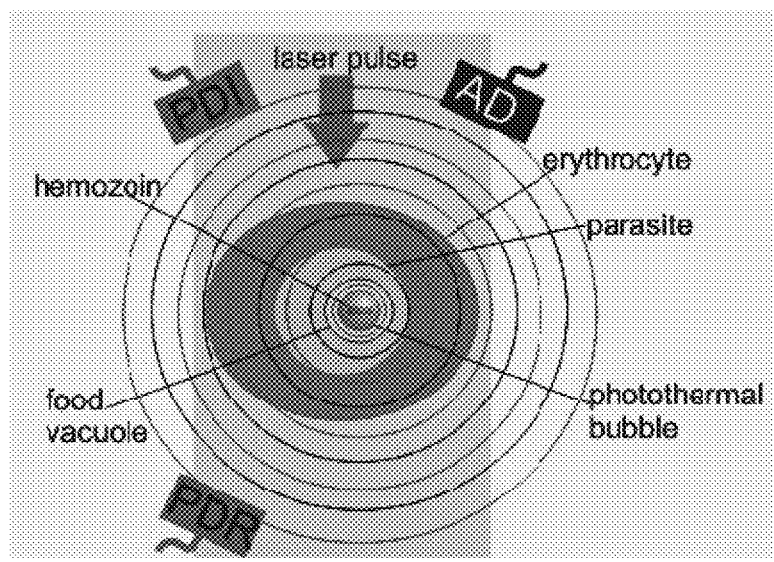

FIG. 4. Principle of diagnostics of malaria and of the guidance of PTNB therapeutics through the detection of PTNBs with three methods: optical scattering of probe laser beam (red) is registered with the image photodetector (PDI) and response photodetector (PDR) as PTNB image and time response, respectively; pressure pulses generated during PTNB expansion and collapse are registered as acoustic time response with acoustic detector (AD).

Figure 5:
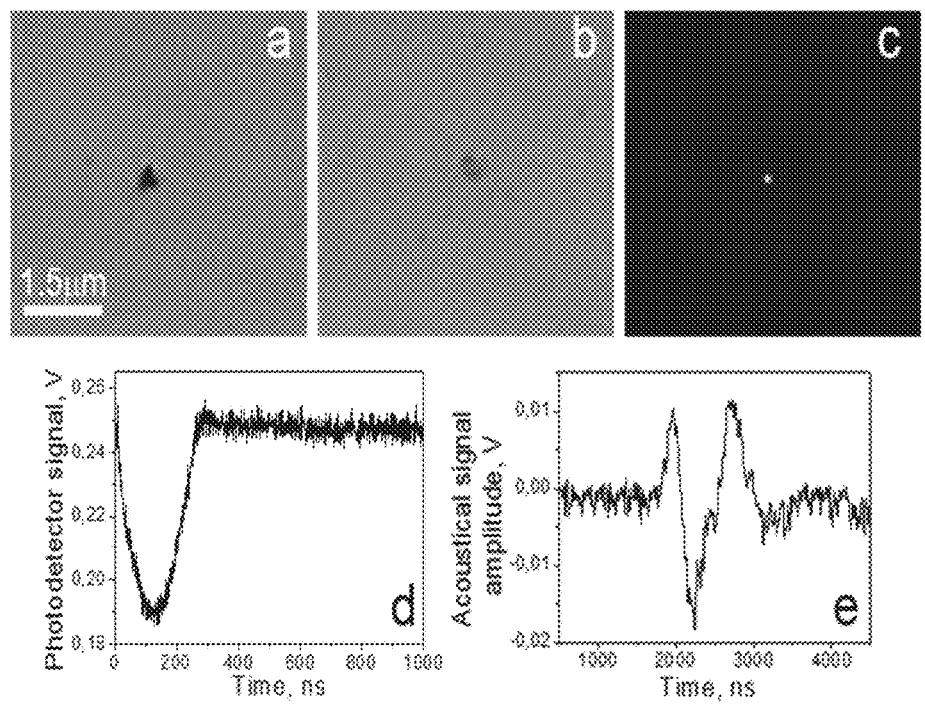

FIG. 5. Response of individual Hz crystal to a single 500 ps laser pulse (532 nm, 30 mJ/cm$^2$): (a) Bright field image of intact Hz crystal; (b) Bright field image of the same Hz crystal after its exposure to a single laser pulse; (c) Time-resolved optical scattering image shows the PTNB (PTNB) generated around Hz crystal during exposure to a single laser pulse; (d) Optical scattering time response of the PTNB obtained simultaneously with the image shown in C, duration of the time-response at the level of 0.5 of the maximum used to measure the lifetime of PTNB.

Figure 6:
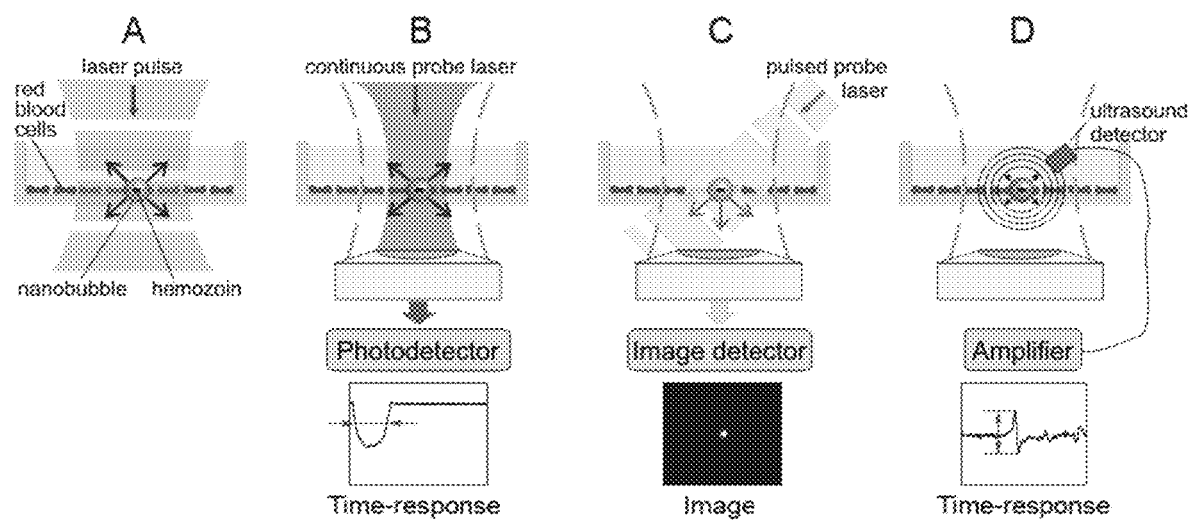

FIG. 6. Experimental set up for excitation and detection of PTNBs with three simultaneous techniques. (a) Generation of a PTNB around a Hz nanocrystal inside the malaria parasite is achieved with a single short laser pulse that is absorbed by the Hz and causes highly localized and rapid heating of the water layer surrounding the object. (b) Optical scattering traces are obtained with a continuous probe laser (633 nm) that is focused into a sample collinearly with the excitation pulse. The scattering effect of the PTNB reduces the axial intensity of the probe beam, which is measured by a fast photodetector. (c) Time-resolved optical scattering imaging employs side illumination with a probe laser pulse (70 ps, 580 nm, 2 nJ) that is delayed for 10 ns relative to the excitation pulse. The probe light is scattered by the water-vapor boundary of the PTNB and generates a distinct image in the microscope. (d) An acoustic trace is obtained with an ultrasound transducer that remotely detects pressure transients emitted during bubble expansion and collapse.

Figure 7:
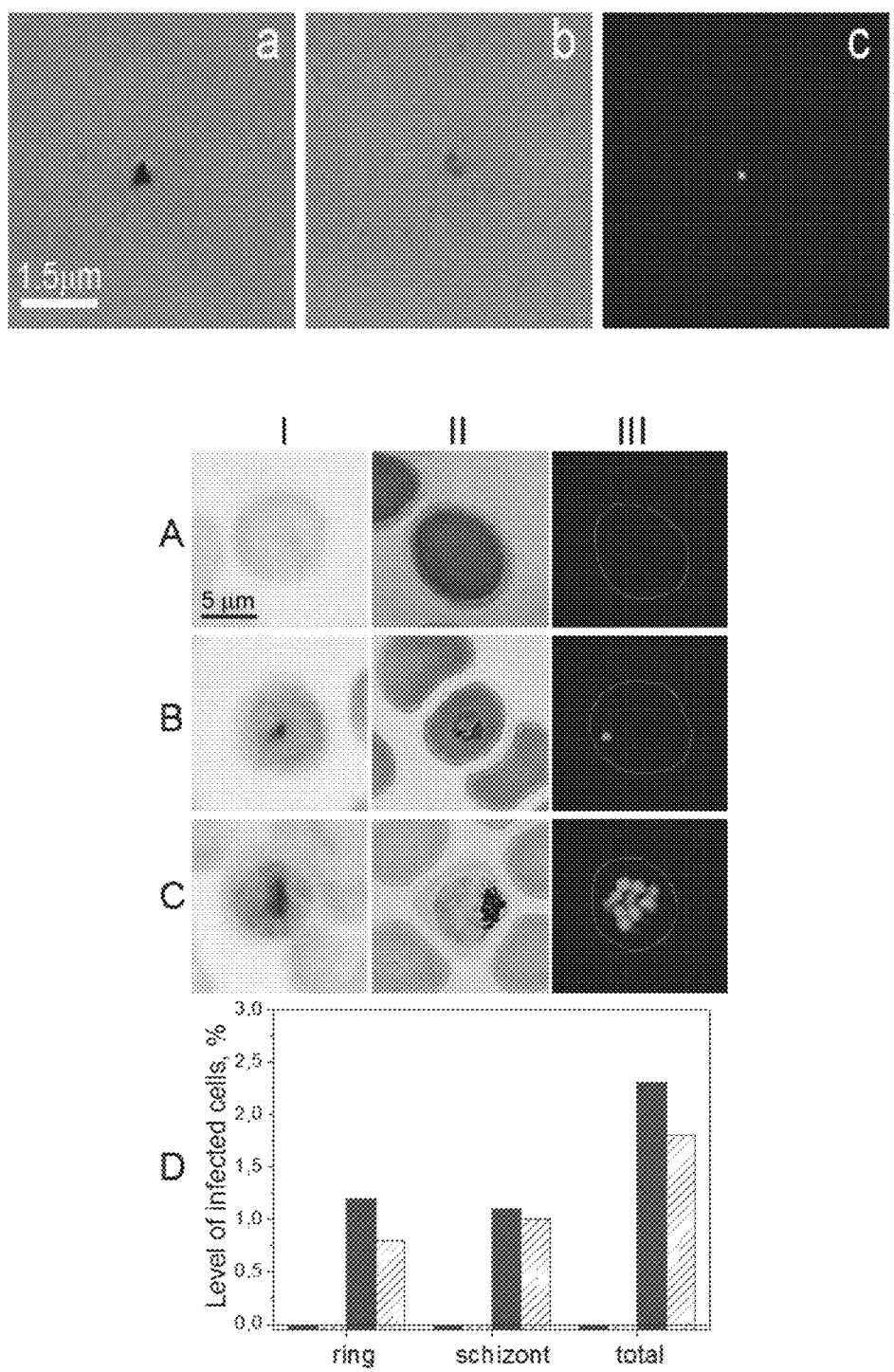

FIG. 7. Images (a-c) and image-based counts (d) of parasite-infected human RBCs stained with Giemsa and SYBR green I fluorescent dye. I: (a) Bright field microscopy images of the Giemsa-stained uninfected cells; (b) early ring stage; and (c) mature schizont stage of malaria parasites. II: Confocal scanning bright field images of the Giemsa-stained cells. III: Confocal scanning fluorescent images of SYBR green I dye-stained cells. (d) Counts of the human RBCs in Giemsa-stained (striped) and SYBR green 1-stained (solid) samples (green, uninfected RBC; blue, MIRBC) for early ring, mature schizont and all stages of development of the malaria parasite.

Figure 8:
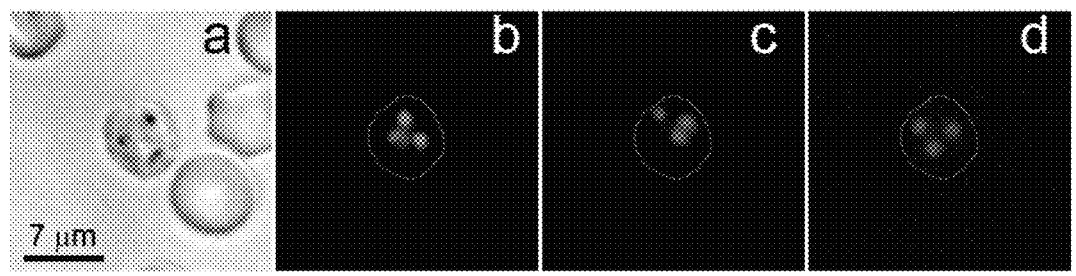

FIG. 8. Influence of the laser-induced PTNB on the location and integrity of SYBR green I-stained malaria parasite in schizont stage of an individual infected RBC. (a) The bright field image of the cell before the laser pulse. (b) SYBR green I fluorescence of the cell before the laser pulse. (c) The same cell immediately after the PTNB generation. (d) The original cellular location 2.5 hours after PTNB generation and explosion.

Figure 9:
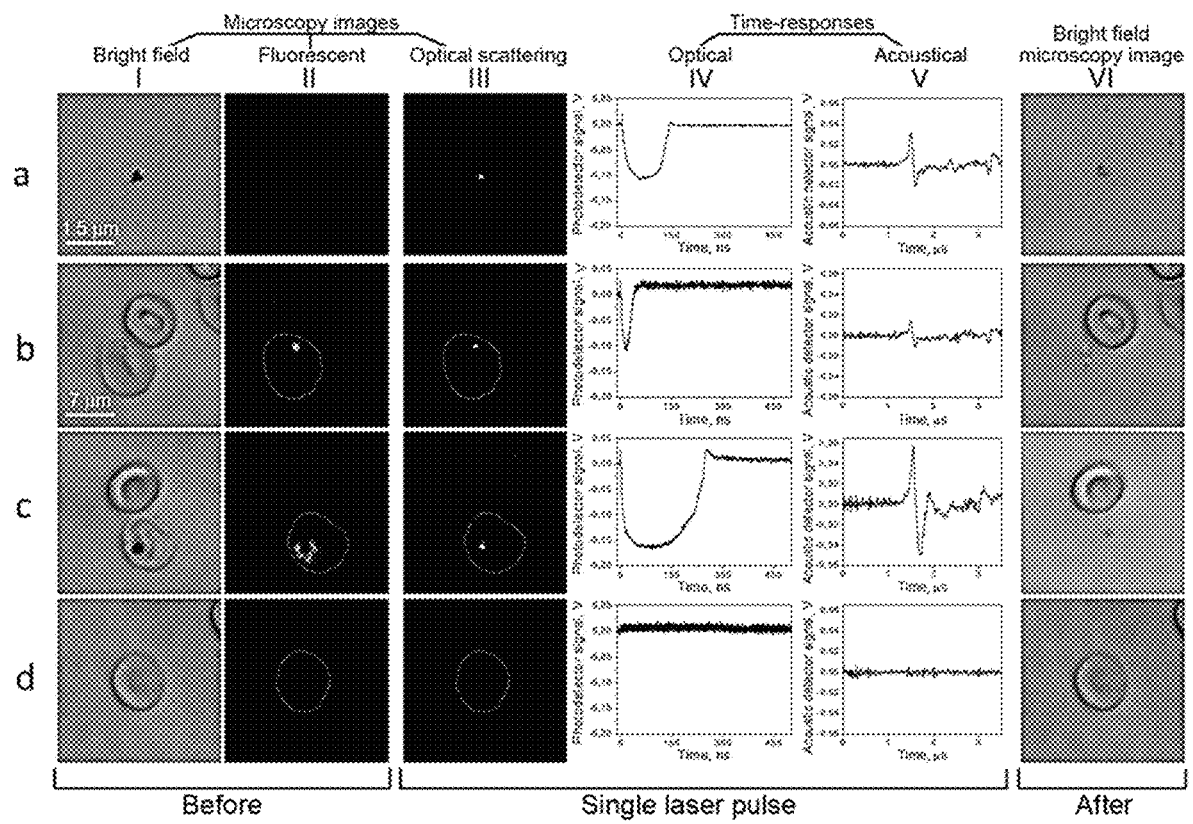

FIG. 9. Pulsed laser exposure of isolated Hz and cultured human blood cells results in Hz-dependent PTNB generation, which is detectable by optical scattering and acoustic signals, and results in infected cell destruction. (a) Hz nanocrystal in water. (b) Uninfected (top cell) and *P. falciparum* early ring-stage infected (bottom cell) human RBCs. (c) Uninfected (top cell) and *P. falciparum* mature schizont stage-infected (bottom cell) human RBCs. (d) Uninfected human RBC. (I) Bright field image shows cells before laser pulse. (II) SYBR green I fluorescence image reveals parasite presence before laser pulse. (III) Time-resolved optical scattering images of PTNBs. (IV) PTNB-induced optical scattering trace (time-response). (V) PTNB-induced acoustic trace (time-response). (VI) Bright field images after laser pulse. Laser pulse was 532 nm, 70 ps, 40 mJ/cm$^2$.

Figure 10:
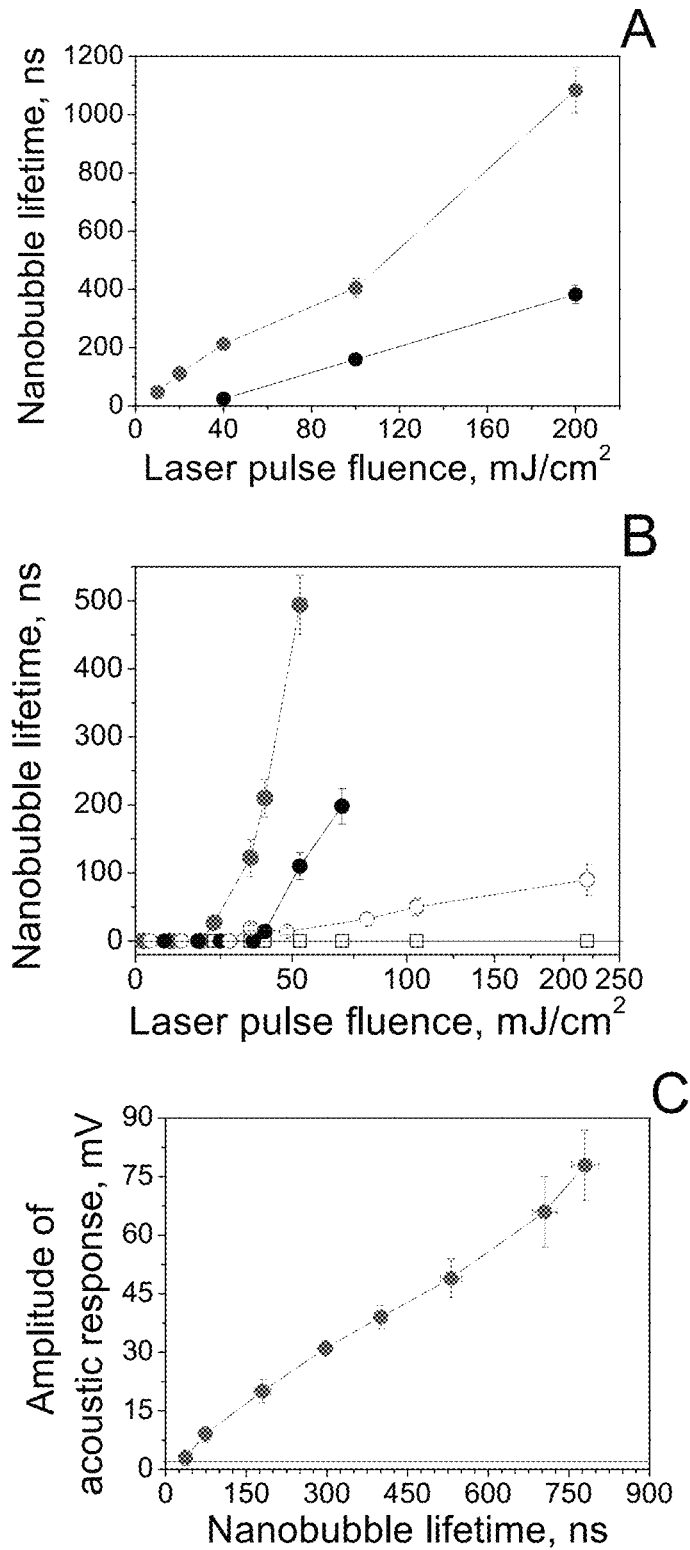

FIG. 10. Parameters of Hz- and laser pulse-induced PTNBs measured by optical and acoustical traces. (a) Dependence of the PTNB lifetime (a metric for maximal size) upon the single laser pulse fluence and duration for Hz crystals in water (red: 532 nm, 70 ps; black, 532 nm, 14 ns (measured by light scattering traces)). (b) Dependence of the PTNB lifetime on laser pulse fluence and duration for uninfected RBCs and for MIRBCs with early ring and mature schizont stages of parasites (solid red: MIRBC, schizont stage, laser pulse at 532 nm, 70 ps; hollow red: MIRBC, ring stage, laser pulse at 532 nm, 70 ps; solid black: MIRBC, schizont, laser pulse at 532 nm, 14 ns; hollow black: uninfected RBC, laser pulse at 532 nm, 70 ps). (c) Amplitude of acoustic trace as a function of the optically measured lifetime for the PTNBs generated in individual MIRBCs.

Figure 11:
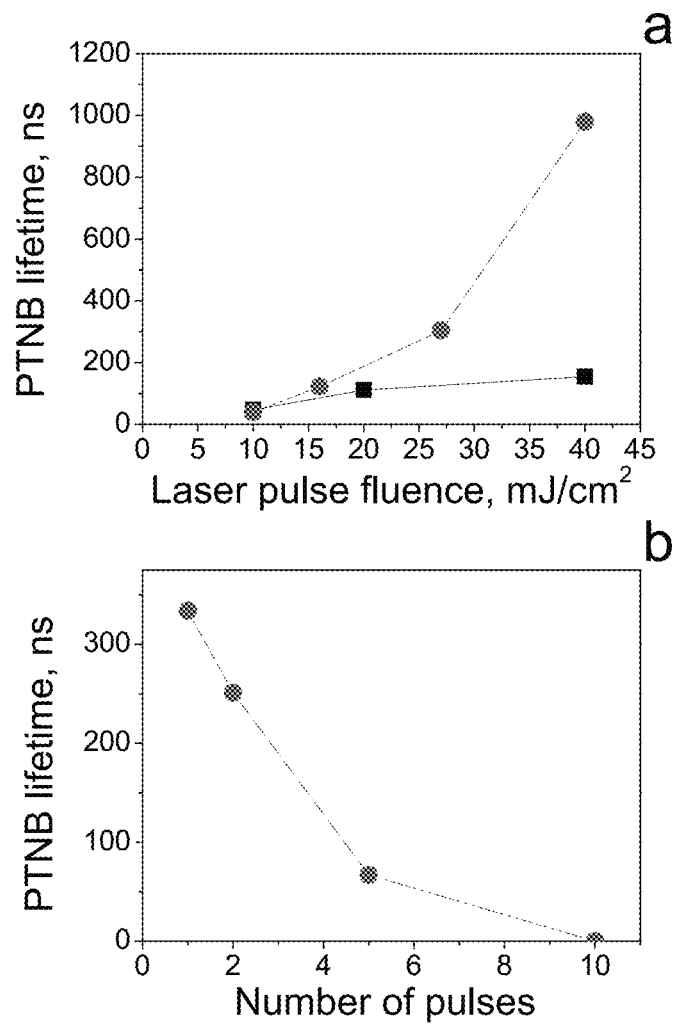

FIG. 11. Dependence of the lifetime of PTNBs generated around individual Hz crystals upon (a) fluence of the laser pulse (two laser pulses of different durations were compared, 70 ps (black) and 500 ps (red)), (b) number of laser pulses (532 nm, 500 ps, 27 mJ/cm$^2$) (decrease of the lifetime correlates with the destruction of the Hz crystal).

Figure 12:
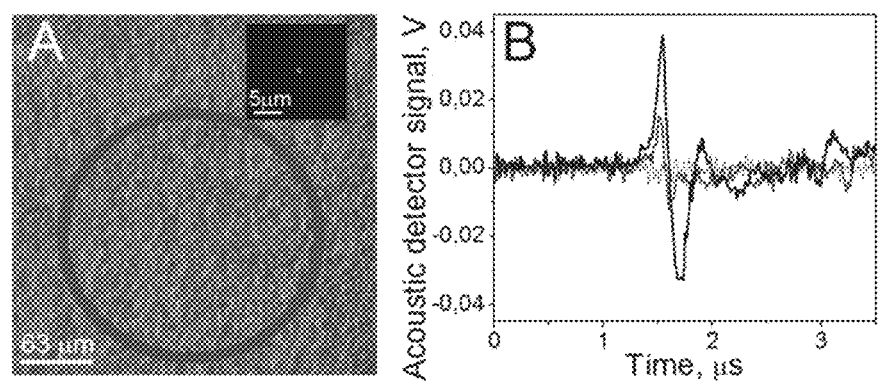
Figure 12:
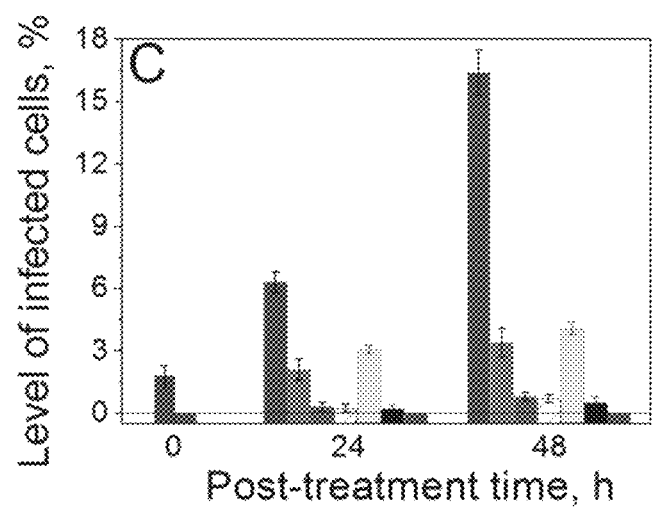

FIG. 12. Diagnostic and parasiticidal effects of PTNBs in *P falciparum*-infected human RBCs exposed to laser pulse in bulk culture. (a) Bulk excitation of ~600-800 cells with a single (532 nm, 70 ps, 50 mJ/cm$^2$) laser pulse of broad aperture to expose cells within an area depicted by the red outline. Inset shows a single ring-stage MIRBC among uninfected cells detected with SYBR green I fluorescence within the laser-exposed area. (b) Acoustic traces resulting from a single laser pulse (532 nm, 70 ps, 50 mJ/cm$^2$) irradiation of cells (green, uninfected RBCs; black, one schizont-stage MIRBC among uninfected RBCs; red, one ring stage MIRBC among uninfected RBCs). (c) Levels of parasitemia: initially (0 hours), 24 hours after laser treatment, and 48 hours after laser treatment (blue, untreated MIRBCs; magenta, MIRBCs treated with laser pulse of 14 ns, 70 mJ/cm$^2$; red, MIRBCs treated with laser pulse of 70 ps, 30 mJ/cm$^2$; red stripes, MIRBCs treated with laser pulse of 70 ps, 130 mJ/cm$^2$; green, normal RBCs; yellow: MIRBCs treated with 1 chloroquine; black, MIRBCs treated with laser pulse of 70 ps, 30 mJ/cm$^2$ and 1 µM chloroquine).

Figure 13:
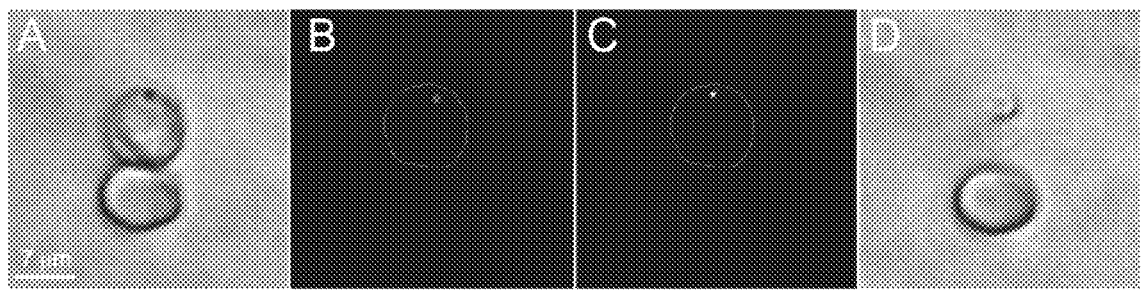

FIG. 13. Localized disruptive effect of laser-induced PTNBs. Images of two RBCs, a MIRBC (top cell) and an uninfected (bottom cell) RBC. (a) Bright field image before the PTNB generation. (b) Fluorescent image of SYBR green I before the PTNB generation. (c) Light scattering imaging of a PTNB after a short pulse laser excitation. (d) Bright field image after PTNB generation.

Figure 14:
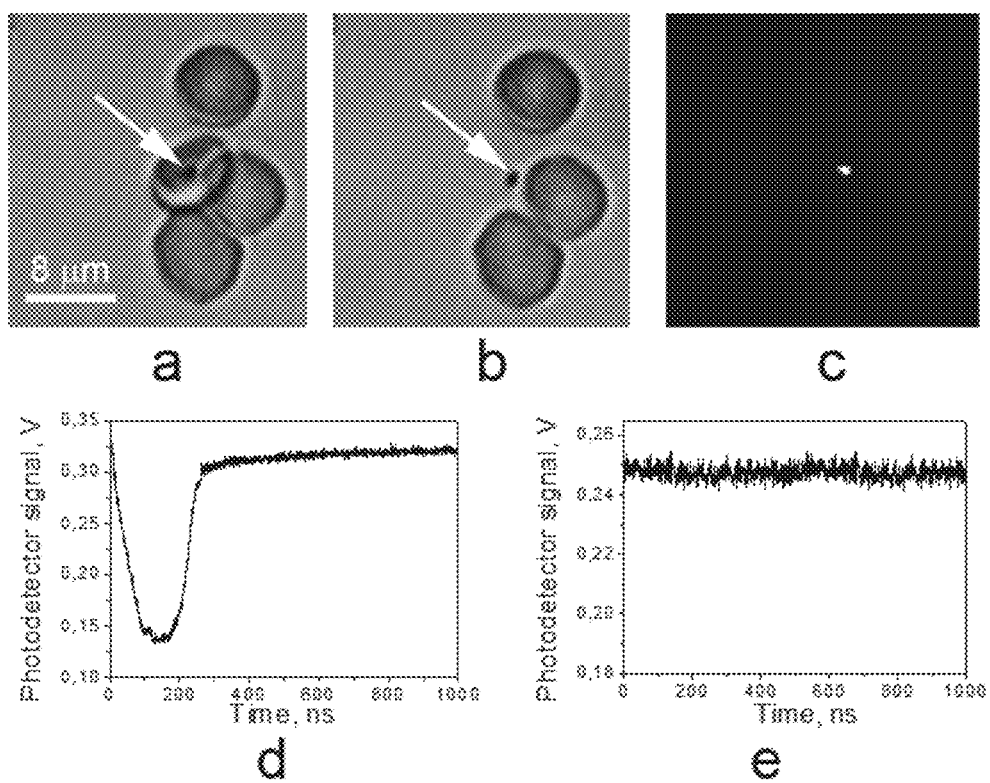

FIG. 14. Responses of human RBCs to a single laser pulse. (a) Bright field image of several intact RBCs (one with HZ crystal as shown by the white arrow). (b) The same cells after exposure to a single laser pulse (532 nm, 500 ps, 31 mJ/cm$^2$). (c) Time-resolved optical scattering image of the same cells shows the PTNB only around Hz crystal. (d) Time-response obtained from the RBC with Hz crystal. (e) Time-response obtained from the RBC without Hz crystals.

Figure 15:
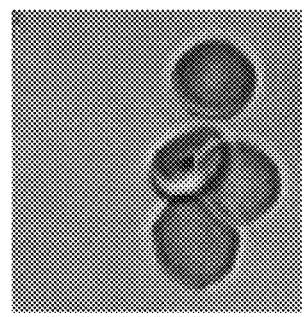
Figure 15:
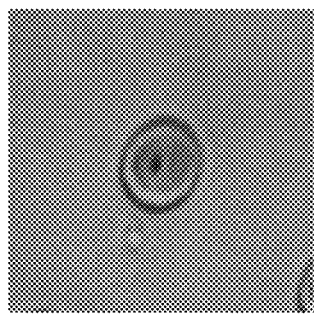
Figure 15:
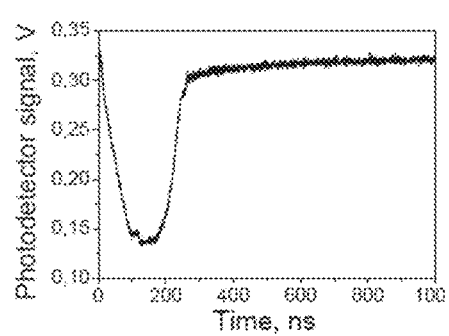
Figure 15:
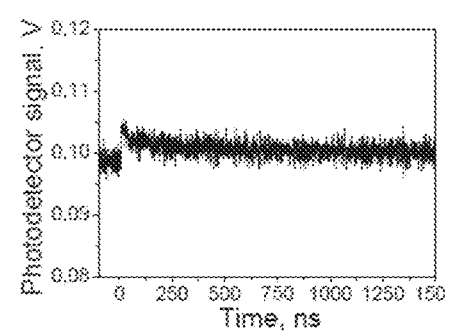
Figure 15:
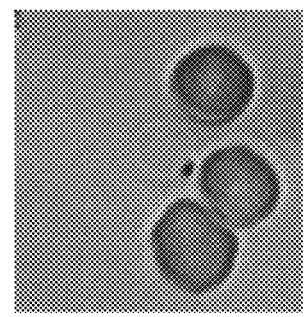
Figure 15:
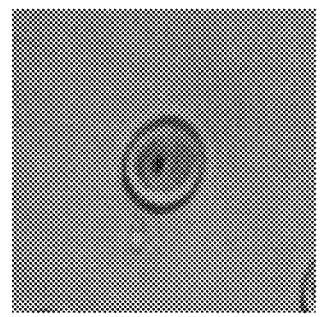

FIG. 15. Comparison of the responses of human RBCs with Hz crystals to the two therapeutic impacts. PTNB (top row, 532 nm, 500 ps, 31 mJ/cm$^2$, single pulse treatment) and hyperthermia (bottom row, 532 nm, 500 ps, 100 mJ/cm$^2$, continuous treatment during 10 s at 10 Hertz and 1 mJ/cm$^2$ per pulse). (a), (b) Intact cells. (c), (d) Time responses show PTNB-specific, see (c), and heating-cooling, see (d), signals. (e), (f) Cells after the treatment.

Figure 16:
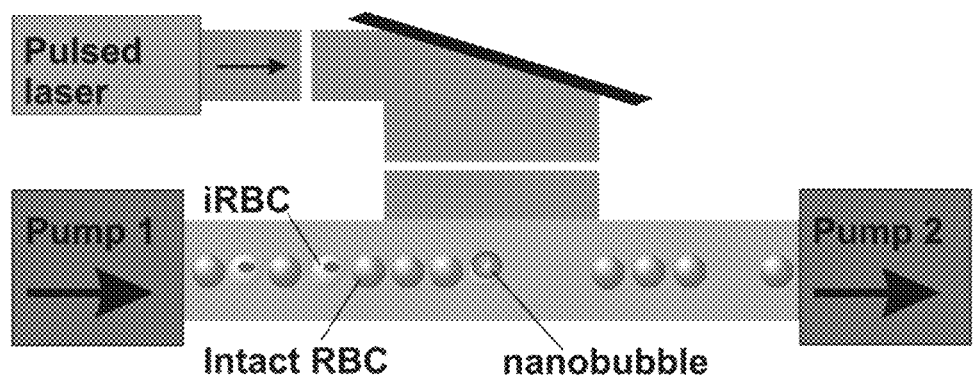

FIG. 16. Experimental scheme for the bulk flow treatment of blood cells with a pulsed broad excitation laser and a flow cuvette with two pumps for dispersing and collecting of blood cells.

Figure 17:
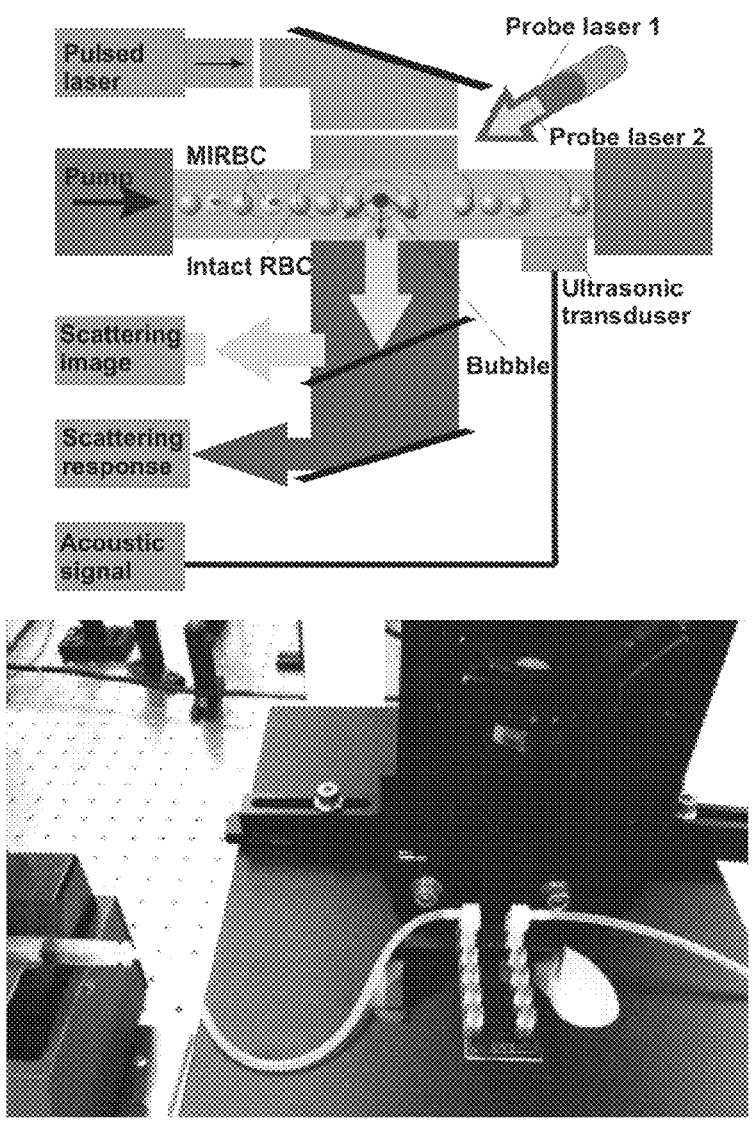

FIG. 17. (a) Functional diagram of the device for malaria diagnostics, therapeutics and theranostics: blood containing uninfected RBCs (blue) and MIRBCs (brown) flows through an optically transparent cuvette where the cell suspension is exposed to short laser pulses of specific energy (green). Generation of PTNBs in MIRBCs are detected optically with the two additional probe lasers (as scattering image with an image detector and as a time response with a photodetector) and acoustically (with ultrasound transducer). Processed blood is collected into a sterile reservoir. (b) An experimental prototype of laser flow system shows the optical set up, transparent flow cuvette and the syringe pump that flows the cell suspension through the cuvette.

Figure 18:
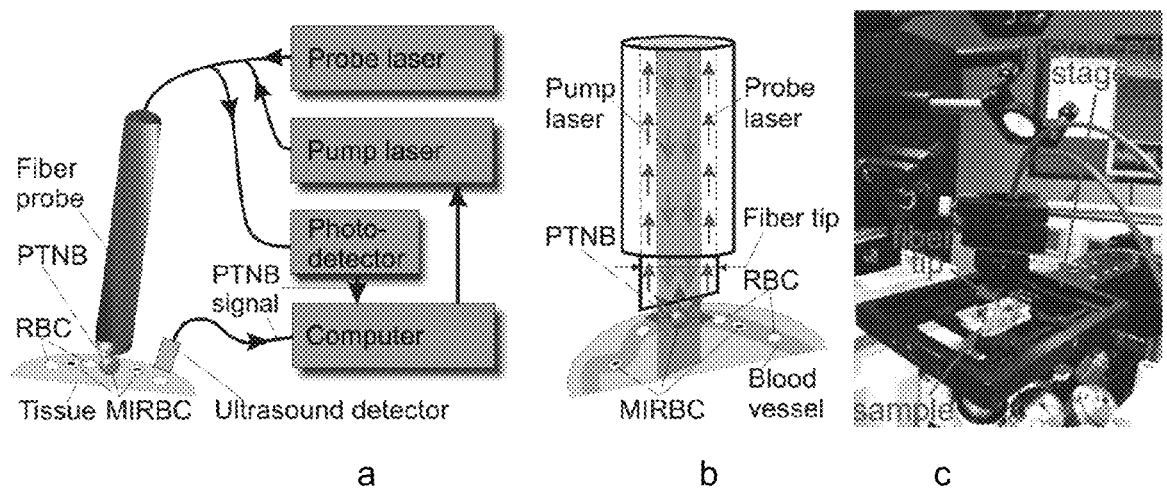

FIG. 18. (a) Functional diagram of the fiber optical system for in vivo diagnosis of malaria: optical fiber probe deliver the excitation laser pulse from the pump laser and collects the light of the probe laser after it is scattered by PTNBs. Collected scattered light is detected by a photodetector. In parallel the PTNB is detected with ultrasound detector. Output signals of the photodetector and ultrasound detector are counted and analyzed by computer algorithm that delivers the diagnsotic data. (b) The mechansim of the PTNB diagnosis of malaria in vivo: the excitation laser radiation is directed with a fiber probe into sub-cutaneous blood vessel where PTNBs are generated in MIRBCs. (c) A photograph of the experimental prototype of the fiber system for PTNB generation and detection.

DESCRIPTION

The present disclosure relates to the field of medical therapies employing nanoparticles and nanobubbles. More specifically, the present disclosure relates to methods, systems, and apparatus for employing nanobubbles for theranostic purposes.

In general, the present disclosure aims, at least in part, to improve the efficacy of the diagnosis and treatment of malaria. Rapid, accurate, and non-invasive detection of low levels of malaria parasites in blood is critical for surveillance, treatment, and elimination of malarial infection. In addition, innovative methods are required to combat growing drug resistance of malaria parasites. Both detection and parasite destruction ultimately need single infected cell sensitivity and specificity, robust inexpensive devices, and minimal dependence upon chemical reagents. None of the existing technologies can rapidly and non-invasively detect and destroy the parasite in a single red blood cell. Thus, the present disclosure aims, at least in part, to improve the efficacy of the diagnosis and treatment of malaria by generating laser-induced photothermal nanobubbles (PTNBs) around malaria-specific nanoparticles. A PTNB may act as a diagnostic and/or parasiticidal agent and may cause destruction of the Hz nanocrystal, the malaria parasite, the malaria infected red blood cell (MIRBC), or a combination thereof.

The present disclosure is based, at least in part, on the photoexcitation of a MIRBC by a short laser pulse causing selective transient heating of a malaria-specific nanoparticle (e.g., a Hz nanocrystal) and resulting in the creation of a transient, water vapor nanobubble, a PTNB, surrounding the malaria-specific nanoparticle. Such bubbles are generated by the nanocrystal's absorption of optical light energy and the resulting overheating and evaporation of the surrounding solvent. The bubbles are termed photothermal nanobubbles due to their optical and thermal origin. The expanding PTNB creates an impact similar to an explosion and can be controlled at nanoscale. This mechanical impact allows for the destruction of the Hz nanocrystal, the malaria-specific parasite, the MIRBC, or a combination thereof. In addition, PTNBs may be detected by one or more optical or acoustic detectors, allowing for the detection of MIRBCs and affording real-time guidance of the application of destructive PTNBs to eliminate the malaria-specific parasite.

In certain embodiments, the present disclosure provides methods for detecting the presence of a malaria-specific nanoparticle, destroying the malaria-specific parasite, and receiving real-time guidance on the destruction of the malaria-specific parasite.

In certain embodiments, the present disclosure provides systems comprising one or more optical detectors capable of detecting the presence of a malaria-specific nanoparticle and a laser capable of generating a short laser pulse sufficient to create a PTNB around the malaria-specific nanoparticle. Some embodiments utilize an acoustic detector in place of any optical detectors, while various embodiments use one or more optical detectors in combination with an acoustic detector.

In certain embodiments, the present disclosure provides an apparatus comprising a means for detecting the presence of a malaria-specific nanoparticle, a means for destroying the malaria-specific parasite, and a means for receiving real-time guidance on the destruction of the malaria-specific parasite.

As used herein, the term malaria-specific nanoparticle refers to a nanoparticle associated with a malaria-specific parasite (e.g. *Plasmodium falciparum*, and other types) having a dimension (e.g., a diameter) of about 1,000 nm or less, and capable of converting electromagnetic radiation into thermal energy. The nanoparticle may have any shape or structure (e.g., spherical, tubular, shell-like, elongated, etc.). In certain embodiments, malaria-specific nanoparticles may be Hz nanocrystals, the tightly packed nanocrystals produced endogenously by the malaria parasite through the parasite's digestion of hemoglobin. Hz nanocrystals have a high optical absorbance, which is significantly higher than that of a normal red blood cell (RBC) and of normal hemoglobin, the major RBC protein. As a result, a Hz nanocrystal can convert the optical energy associated with a short laser pulse into heat and can generate a localized transient PTNB within a malaria parasite located in a MIRBC. Thus, in certain embodiments, unlike many current malaria treatments that combat a parasite by preventing Hz formation, Hz nanocrystals may be used as an "Achilles heel" to facilitate parasite detection and destruction. In some embodiments, the malaria-specific nanoparticles may be exogenously added nanoparticles with appropriate photothermal properties (e.g., gold nanoparticles) conjugated to malaria-specific antibodies.

As used herein, the terms nanobubble and PTNB refer to the transient vapor bubble that emerges around a nanoparticle when it is locally and transiently heated by exposure to electromagnetic radiation. The nanoparticle itself may not evaporate, instead acting as a heat source and heat accumulator in an intricate process of heat transfer and phase transition in the nanoparticle environment at nanoscale. The PTNB expands rapidly to its maximal diameter and then collapses with its lifespan being longer than the duration of radiation pulse that feeds the energy to the bubble through the nanoparticle. Thus, a PTNB results when a nanoparticle evaporates a very thin volume (nanometer size) of the surrounding medium, creating a PTNB that expands and collapses within a short nanosecond. The PTNB's rapid expansion produces a localized mechanical and non-thermal impact that may result in damage or destruction to cellular components or to the cell itself.

By way of explanation, PTNBs allowed for, among other things, higher parasiticidal efficacy, shorter treatment time, and lower optical dose of the treatment as compared to a hyperthermia approach. Thus, PTNBs are particularly suited for treatment of MIRBCs because they allow for parasiticidal efficacy while minimizing destruction of uninfected RBCs, due, for example, to delocalized photothermal heating.

In certain embodiments, malaria-specific nanoparticle (e.g., Hz nanocrystals) act as photothermal targets within MIRBCs or other malaria-infected tissues and cells. In particular embodiments, selective laser pulse-induced heating of a malaria-specific nanoparticle causes generation of a PTNB. Generation of a PTNB around optically absorbing objects, such as Hz nanocrystals, assumes a transient localized evaporation of the liquid media around the object. Rapid heat transfer from the laser-excited optical absorber raises the temperature of the surrounding solvent layer above its evaporation threshold, with the simultaneous buildup of the internal vapor pressure. When the pressure inside the evaporated layer exceeds the external pressure of the surface tension at the boundary of the vapor inside and bulk liquid outside, the PTNB begins to expand rapidly, with speeds ranging from 10 meters per second to 100 meters per second, until the bubble reaches a maximal diameter that corresponds to a transient equilibrium, when the internal and external pressures are equal. Because, in some embodiments, PTNB generation is induced by a single short pulse, the bubble has no continuing source of internal energy, and will therefore eventually depressurize and collapse back to the nanocrystal that generated it. The maximal size of the PTNB is determined by the thermal energy that is generated from light absorption by the Hz nanocrystals. In certain embodiments, a PTNB diameter may be sufficient to destroy a malaria-specific parasite. For example, the PTNB diameter may range in size from 100 nanometers to tens of micrometers. The duration of the expansion-collapse cycle determines the lifetime of the PTNB, from 10 nanoseconds to microseconds, and is proportional to its maximal diameter, which is used as the main metric of the PTNB.

Efficient and ultrafast heating of the liquid surrounding the malaria-specific nanoparticle is required to minimize energy dissipation by thermal diffusion. Efficient nanobubble formation is achieved through a fast deposition of light energy into the strongly absorbing malaria-specific nanoparticle (e.g., Hz nanocrystals) with a short laser pulse. In certain embodiments, the PTNB may be formed through a short laser pulse. The laser pulse should be of sufficient energy and duration to form a photothermal nanobubble with a diameter sufficient to cause mechanical destruction of a malaria-specific parasite. Suitable laser pulses may be delivered using, for example, high energy pulsed picosecond laser. In certain embodiments, the laser pulse may have a duration of from 1 picosecond to 100 nanoseconds. The particular laser pulse duration may depend on, among other things, the particular laser chosen.

In certain embodiments, suitable laser pulses may be determined with reference to the characteristic cooling time due to the thermal diffusion is determined by the diameter d of the heated object:

$$\tau = \frac{d^2}{27a}$$

where a is the thermal diffusivity of the environment of the object. Here, we assume that a equals the thermal diffusivity of water, $1.4 \times 10^5$ μm²/second. The sizes of Hz nanocrystals are reported to range between 50 nanometers and 1000 nanometers with the smallest crystals being formed during the early ring stage of the malaria parasite. This reported size range predicts cooling times for the Hz absorbers between 0.5 nanoseconds and 26 nanoseconds. Therefore, to ensure rapid enough energy deposition to create a PTNB, and to minimize thermal diffusive losses, rather than simple heating, in certain embodiments a 70 picosecond pulsed laser (e.g., PL-2250, Ekspla, Vilnius, Lithuania) and/or a 14 nanosecond pulsed laser (e.g., Nd-YAG laser LS-2145T, Lotis TII, Minsk, Belarus) may be employed. An optical microscope-based experimental set up, known in the art, may be used to mount and position samples of malaria-specific nanoparticles with a motorized microscope stage (e.g., 8MT167-100, Standa Ltd., Vilnius, Lithuania), operated via custom-made LabView modules (e.g., National Instruments Corporation, Austin, TX). In single cell experiments performed in accordance with certain embodiments, the excitation laser pulse may focused down to a 15 μm area in the sample plane, providing uniform exposure of the entire RBC (diameter 7 μm). In bulk, cultured cells experiments performed in accordance with certain embodiments, the diameter of the excitation laser beam may be increased to 210 μm, providing simultaneous exposure of a monolayer of 600-800 cells by a single laser pulse. Spatial intensity profiles of both beams are Gaussian and their fluence may be measured at the sample plane. The fluence of each single laser pulse may be controlled with a polarizing attenuator and may be measured by registering the size of the image of the laser beam at the sample plane with an EM CCD camera (e.g., Luka model, Andor Technology, Northern Ireland). The pulse energy may be assessed with an energy meter (e.g., Ophir Optronics, Ltd., Israel). The fluence may be calculated using the pulse energy and the laser beam image size, with the beam diameter measured at the level of $1/e^2$ relative to the maximum. In accordance with various embodiments, each MIRBC may be positioned into the center of laser beam and may be exposed to a single pulse at a specific fluence.

The duration of a 70 picosecond pulse is much shorter than the estimated cooling times (due to, e.g., thermal dissipation), and, therefore, such pulse durations should provide very localized heating with minimal dissipation (due to, e.g., diffusion) of heat during the deposition of optical energy into the Hz nanocrystal. In certain embodiments, the excitation wavelength is a wavelength where a malaria-specific nanoparticle shows relatively high optical absorbance (See e.g., FIG. 1). For example, the excitation wavelength may be approximately 532 nanometers, a wavelength where Hz shows relatively high optical absorbance. In other examples, the excitation wavelength may have a value in the range from 400 to 1000 nanometers. For example, the excitation wavelength may have a value of 650 nanometers. Unlike hemoglobin, Hz does not have sharp specific spectral peaks, but nevertheless, its optical absorbance is five- to seven-fold higher than that of hemoglobin in RBCs. This large difference enables selective photothermal generation of PTNB around Hz nanocrystals in accordance with particular embodiments, without inducing vapor bubbles or significant heating in uninfected RBCs.

In various embodiments, the maximal size of a PTNB is determined by the optical energy transmitted to a malaria-specific nanoparticle by a laser. Increasing the optical energy increases the maximal size of the PTNB. Mechanical destruction caused by the PTNB depends on its maximal size. In certain embodiments, this rapid expansion and collapse may destroy the nanoparticle, the food vacuole of the malaria parasite, the malaria parasite itself, or the MIRBC depending on the maximal diameter of the PTNB. The maximal diameter of the PTNB corresponds to the energy received by the malaria-specific nanoparticle from a laser or other source of electromagnetic radiation. Thus, the generation of PTNB around the malaria-specific nanoparticle requires a small energy pulse, destruction of the food vacuole requires an increase in the energy of the laser pulse, destruction of the parasite itself requires another energy increase, and destruction of the MIRBC requires an even higher energy pulse. Destruction of the MIRBC assumes that all internal components are also destroyed.

In certain embodiments, malaria may be diagnosed through one or more optical detectors, an acoustic detector, or both, by detecting the presence of PTNBs generated around Hz nanocrystals present in malaria-specific parasite. A PTNB generated by the short laser pulse may be detected with a low intensity continuous probe laser that measures the strong optical scattering produced by the expansion and collapse of nanobubbles using a photodetector. Optical scattering changes will only occur in MIRBCs containing malaria-specific nanoparticles (e.g., Hz nanocrystals) and thus, are diagnostic of malarial infection. Optical scattering signals of PTNB may be registered in various embodiments in several ways, including, as a time-resolved optical scattering image that will show the presence of transient PTNBs and as an optical scattering time-response that will measure the maximal diameter and lifetime of the PTNB. The maximal diameter determines the optical properties of the PTNB. In certain embodiments, the generation of even a single PTNB in a single MIRBC may be detected acoustically, because the PTNB emits a pressure pulse that may be detected independently or in parallel with an optical signal of the bubble from an ultrasound transducer. Thus, certain embodiments of the present disclosure provide at least three independent techniques for a real time detection of Hz nanocrystals with cell sensitivity. In particular embodiments, the diagnostic sensitivity of these embodiments may range from detecting 1 MIRBC in $10^4$ uninfected RBCs to 1 MIRBC in $10^8$ uninfected RBCs, and, in particular, may range from detecting 1 MIRBC in $10^6$ uninfected RBCs to 1 MIRBC in $10^8$ uninfected RBCs, thus outperforming current methods of diagnosis. In addition, the PTNB diagnostics method of particular embodiments may employ real time signal detection, and thus diagnosis may take only seconds. As a result, advantages of certain embodiments over previous diagnostic attempts using Hz nanocrystals may include heightened sensitivity and the ability to conduct in vivo or single cell testing, even in the early ring stage of the malaria parasite, using a rapid label- and needle-free procedure.

In certain embodiments, optical or acoustic signals, or both, may also guide the therapeutic use of PTNB generation. From a therapeutic perspective, the bulk laser pulse treatment of human blood in accordance with various embodiments results in PTNB-induced explosive mechanical destruction of up to 95% of malaria parasites, while leaving uninfected cells undamaged. This provides a significant advantage over previous attempts to use photothermal destruction of MIRBCs that relied on pre-treating MIRBCs with an absorbing dye and used a much longer pulse and 1000-fold higher energy, resulting in low selectivity of MIRBCs for destruction and damage to uninfected RBCs. The disclosed embodiments also provide advantages over previous attempts to use magnetic heating of Hz to destroy malaria parasites, which suffered from significant thermal diffusive losses due to long excitation times leading to reduced efficacy and selectivity. In contrast, the short, low energy laser pulses disclosed herein, in accordance with particular embodiments, provide only localized mechanical impact and single cell selectivity without heating or damaging uninfected cells.

Since diagnostics and therapeutics are supported by the same PTNB-based process, in particular embodiments, they may be united into one connected and fast theranostic procedure that may detect, destroy and simultaneously guide in real time the destruction of malaria parasites with single cell selectivity and nanosecond speed. In various embodiments, such a theranostic protocol includes: detection of Hz nanocrystals, which are indicative of the presence of the malaria parasite, by generating PTNB-specific optical and acoustic signals for diagnosis of malaria infection; selective destruction of the parasite using a short laser pulse to locally destroy the parasite as a therapy; and real time guidance of the destructive PTNBs with the optical and acoustic signals coming solely from MIRBCs.

In certain embodiments, the device that supports a theranostic method may comprise an optically transparent cuvette of specific dimensions in combination with a pump that provides the flow of blood cells through the cuvette in such a way that all cells form a two-dimensional monolayer that can be exposed by a pulsed laser radiation. By means of example, and not limitation, such cuvette may include an optically transparent segment 2 cm wide, 10 cm long and 200 μm high, while the pump provides the blood flow speed in the range from 1 cm/c to 10 m/s. Certain embodiments may comprise an excitation pulsed laser with the pulse duration below 20 ns, wavelength ranging from 400 nm to 1200 nm, pulse fluence that can be tuned in the range from 10 mJ/cm$^2$ to 500 mJ/cm$^2$, and pulse repetition rate in the range from 1 hertz to 10 kilohertz. Various embodiments may comprise a continuous probe laser of any wavelength with the power being low enough to avoid heating any Hz nanocrystals, but sufficient to provide the detection of a portion of the optical radiation being scattered by a single PTNB. The probe laser may illuminate the same area of the cuvette as the excitation pulsed laser beam. Certain embodiments may comprise an optical detector of any type that can detect the portion of the radiation of the probe laser being scattered by a single PTNB. Speed (temporal resolution) of such photodetector and associated signal analyzer should provide the detection of a single signal pulse with duration from 10 ns to 1000 ns. Particular embodiments may comprise an acoustic detector of any type that can detect a pressure pulse emitted by at least a single PTNB in the area exposed to the excitation pulsed laser.

In various embodiments, the device comprises an optical fiber probe capable of delivering an excitation laser pulse from the pulsed laser and collecting the light of the probe laser after it is scattered by PTNBs. In various embodiments, the optical fiber probe also comprises a photodetector capable of detecting the collected scattered light. In particular embodiments, PTNBs may be detected in parallel with an ultrasound detector. Certain embodiments may count and analyze output signals of the photodetector and ultrasound detector through a computer algorithm that delivers the diagnostic data. Aspects of these embodiments may be used together or separately and may be appropriate for in vivo application.

In certain embodiments, the malaria-specific nanoparticle may be an exogenously added photothermal agent, such as a gold nanoparticle conjugated to a malaria-specific antibody. Malaria-specific antigens expressed at the membrane of MIRBCs may be used to selectively target gold nanoparticles to MIRBCs. Such short pre-treatment of blood opens the following opportunities for improving the treatment of malaria by generating laser-induced generation of PTNBs that will be large enough to destroy the parasite in MIRBCs selectively and rapidly during single pulse treatment. In some embodiments, laser-induced generation of small PTNBs could also be used for intracellular delivery of anti-malaria drugs that otherwise have limited targeting efficacy against malaria by selectively opening liposome vesicles containing the drugs and attached gold nanoparticles.

In certain embodiments, malaria parasites may be detected and destroyed in vivo. In some cases MIRBCs with parasites may adhere to blood vessel walls (due to the interaction of adhesive nobs with endothelial receptors) and as a consequence, these MIRBCs cannot be accessed via extra-corporeal treatment making in vivo detection and destruction advantageous. The mechanism of PTNB-based theranostics can be employed in vivo as well as ex vivo and by using a fiber optical catheter for delivery and collection of laser radiation. The level of laser fluence required for PTNB generation is within the safety limits (25-40 mJ/cm$^2$) established for in vivo use of pulsed laser radiation. In certain embodiments, the performance of PTNB in vivo may be further improved by optimizing the excitation wavelength in the Hz-specific range, approximately 640-660 nanometers, where blood and tissues have better transparency than at 532 nanometers. In some embodiments, an optical catheter may be used for the delivery of the excitation and probe laser radiation and for collection of the light scattered by PTNBs. In particular embodiments, the PTNB diagnostic mode may utilize acoustic detection of PTNBs with a sensor attached outside to the body of a patient. In various embodiments, the optical fiber may be employed only for the delivery of the excitation laser radiation. Besides intravascular delivery, in certain embodiments, the fiber may be directly brought to specific localized target by using a biopsy needle as a guide for optical fiber.

Further, in certain embodiments, PTNBs may be generated around Hz nanocrystals and detected in vivo in a non-invasive way for the purpose of diagnostics alone. In cases where a blood vessel is located very close to a surface (e.g., in the ears, eyes, lips, etc.) the excitation laser radiation may be delivered from an external source through the skin and through a vessel wall. A PTNB may be generated when a MIRBC flows into the irradiated zone and emits an acoustic pulse that may be detected by an acoustic sensor attached to the skin. In various embodiments, delivery of laser radiation may occur through a free space set up or with a fiber optical system that includes a fiber probe whose tip is brought into a contact with skin at the point closest to the target blood vessel. Optical and acoustic transmittance between the probe, sensor and skin may be enhanced by using existing transparent gels. Signals associated with Hz-generated PTNBs may be detected and counted over a specific time. In particular embodiments, such signals may detect a single MIRBC. Small blood vessels have blood flows of over $10^9$ RBCs per minute (less than 1 mL of blood). Therefore, by detecting, for example, 100 PTNB signals, various embodiments may achieve a diagnostic sensitivity of 1 MIRBC per $10^7$ normal RBCs over a 1 minute period. These parameters significantly surpass the performance of many current diagnostic methods. In addition, due to the small laser-irradiated volume required for various embodiments, the energy required for a laser pulse may be reduced resulting in much lower price to create an embodiment.

Various embodiments of the present disclosure present technical advantages over current malarial diagnostic and treatment procedures by detecting and/or destroying any stage (including gametocytes) and any type of malaria parasite that contains Hz nanocrystals. The present disclosure thus supports early-stage diagnosis, fast screening, and monitoring of residual parasites. In particular, from a diagnostic perspective, various embodiments may detect minor amounts of Hz nanocrystals in individual cells and may significantly improve the sensitivity and specificity of malaria diagnosis, detecting 1 MIRBC among $10^{4-8}$ normal (non-infected) RBCs. Moreover, as discussed previously, the time required to diagnosis malaria utilizing various embodiments is meaningfully reduced. The increase in sensitivity and reduction in time for certain embodiments provides an improvement over existing technology. Various embodiments may provide significant therapeutic advantages as well. To date there is no absolutely efficient drug that cures malaria, given at least the problems associated with drug resistance, non-specific targeting of drugs, intracellular location of the malaria parasite, toxicity of the drugs and lack of understanding of all biological malaria-related mechanisms that are targeted by drug therapies. The technical advantages of certain embodiments of the present disclosure may include the ability to combine diagnostics and therapeutics into one connected theranostic procedure. Particular embodiments may include a field diagnostic device that operates in a "one button-one reading" mode, for example by delivering results in seconds by trans-cutaneous generation and detection of PTNB in blood vessels, and that does not require high technical expertise or use any reagents or needle. This embodiment may allow for increased screening of at-risk populations "in the field," i.e., in settings remote from established health care facilities. The present disclosure may also allow for non-invasive monitoring of traditional treatments and/or the in vivo monitoring of the efficacy of new drugs and vaccines.

To facilitate a better understanding of the present disclosure, the following examples of certain aspects of some embodiments are given. In no way should the following examples be read to limit, or define, the entire scope of the disclosure.

EXAMPLES

Optical absorbance. MIRBCs contain a malaria-specific photothermal target, Hz nanocrystals, that have a significantly higher optical absorbance than that for normal (i.e., uninfected) RBC and normal hemoglobin (Hb), the major RBC protein (FIG. 1). As a result, the Hz nanocrystal may be used as localized optical nano-target for selective laser pulse-induced heating and PTNB generation, resulting in localized and selective destruction of the target itself, the plasmodium parasite and the MIRBC without damage to normal RBCs that may be exposed to identical treatment.

Laser pulse heating of hemozoin. Photo-excitation of the MIRBCs by a short laser pulse causes selective transient heating of Hz crystals due to its high optical absorbance (compared to any other molecular optical absorbers in normal blood) and formation of localized PTNB (FIG. 2). Short pulse excitation of Hz will prevent heat losses from the crystal and damage to the host RBC and its environment. Instead, the short mechanical explosive action of the PTNB will, depending upon the maximal diameter of PTNB, locally disrupt and destroy the Hz crystal (smallest PTNB), the food vacuole in which the crystals are found (larger PTNB), and then the malaria parasite itself (PTNB), providing a therapeutic effect, without damaging the host RBC (FIG. 2a-d). The maximal diameter of the PTNB is determined by the energy (fluence) of the excitation laser pulse (FIG. 3). Larger PTNBs generated by more intense laser pulses will destroy all the above-mentioned components and the MIRBC itself. Destruction of either the intracellular parasite or the infected cell will provide a therapeutic effect.

Detection of hemozoin: optical and acoustic signals. Optical scattering and acoustical emission by laser induced PTNBs will allow highly sensitive detection of Hz nanocrystals (FIG. 4). Response of individual Hz crystals to single short laser pulses was studied in standard phosphate buffer suspension (PBS) of Hz (#tlrl-hz, InvivoGen, San Diego, California) prepared at the concentration of 10 μg/mL. Individual crystals were identified though optical scattering images and were positioned into the center of the excitation and probe laser beams. Each Hz crystal (FIG. 5a) was exposed to a single excitation pulse at specific fluence and the data for 30 different crystals (exposed to identical laser pulses) were averaged and analyzed. We observed PTNB-specific optical scattering images (FIG. 5c) and time-response (FIG. 5d) at fluences greater than 10 mJ/cm². Therefore, Hz crystals were able to generate PTNBs even at low optical energies (fluences). Some Hz crystals survived the first pulse and were able to generate the bubbles after being exposed to additional pulses. However, as a rule we observed the destruction and disappearance of the Hz crystal after the first laser pulse (FIG. 5b). In addition to optical detection of PTNBs generated by Hz crystals, we registered acoustic time responses of PTNBs (FIG. 5e).

Detection, imaging, and quantification. In some of our experimental work, detection, imaging, and quantification of PTNBs were performed simultaneously with the excitation pulse using three independent methods. Time-resolved optical scattering imaging (FIG. 6c) shows the PTNB and its spatial location, while optical scattering (FIG. 6b) and acoustic (FIG. 6d) traces are employed to measure the lifetime of the PTNB. The lifetime of the PTNB is proportional to its maximal diameter. In previous work, we have shown that PTNB lifetimes correlate with favorable diagnostic and therapeutic effects where similar PTNBs were generated in cancer cells targeted with gold nanoparticles. Optical detection is based on the excellent light scattering properties of the PTNBs. Acoustic detection is based on the generation of the pressure transients during the bubble expansion and collapse, complements light scattering detection, and, most importantly for diagnostic application, can be used for in vivo detection of PTNBs in opaque tissue.

Light scattering time-responses were measured as integral scattering effects of the PTNB on the continuous probe laser beam that was focused onto the sample collinearly to the excitation laser beam (FIG. 6b). A continuous probe laser beam of very low power (633 nm, <0.1 mW, 05-STP-901, CVI Meller Griot, Albuquerque, NM) was focused at the sample (FIG. 6b) and its axial intensity was monitored with a high-speed photodetector (FPD510-FV, Thorlabs Inc., Newton, NJ) connected to a digital oscilloscope (X42, Lecroy Corporation, Chestnut Ridge, NY) that was synchronized with the excitation lasers. The scattering of the probe laser beam by the PTNB reduces the axial intensity of the probe laser and results in a dip-shaped trace that showed the expansion and collapse of the PTNB as a bubble-specific time course (FIG. 6b). The duration of scattering trace is measured at the half level of its minimum with 0.4 ns resolution and is defined as a lifetime of the PTNB. The probability of PTNB generation is measured as the ratio of PTNB-positive events (objects) (M) to the total number of the objects (N) exposed to the laser pulse:

$$PRB = \frac{M}{N}$$

The level of laser pulse fluence that corresponds to the PRB of 0.5 was determined as the threshold of the PTNB generation.

Time-resolved scattering images (FIG. 6c) were obtained with a short laser pulse (576 nm) delayed for 10 ns relative to the excitation pulse to allow formation and expansion of the PTNB (FIG. 6c). This probe laser side-illuminates the sample so that only light scattered by the PTNB is collected by the microscope objective lens and projected onto an image detector (Luka model, Andor Technology, Northern Ireland). The image of the PTNB is then used to determine the location of the PTNB relative to the malaria parasite whose location is determined with fluorescent microscopy imaging using a parasite-specific SYBR green I fluorescence dye as discussed herein.

Acoustic traces (FIG. 6d) were detected at the distance of several millimeters from the sample with an ultrasound transducer XMS-310 (Olympus NDT Inc., Waltham, MA) coupled to the oscilloscope (X42, Lecroy Corporation, Chestnut Ridge, NY) through an amplifier (Ultrasonic Preamp 5676, Olympus NDT Inc., Waltham, MA). The transducer head was immersed into the cell suspension and was directed toward the exposed area at the distance of approximately 2-3 mm. Pressure transients generated during the expansion and collapse of the PTNBs produce compression-rarefaction type traces that are quantified from their maximal amplitudes.

All three types of signals were recorded simultaneously during exposure of each object to a single laser pulse. The study of each individual cell or the ensemble of the static cells involved the following protocol:

A cell (a field) was positioned into the center of laser beam.
A bright field image of the cell was obtained.
A SYBR green I fluorescent image was obtained.
A single laser pulse was applied at specific duration and fluence.
The three PTNB signals were simultaneously recorded by using the excitation laser pulse to trigger the image detector (see below) and the oscilloscope to record the light scattering and acoustic signals.
Ten nanoseconds after the trigger pulse, a bright field image of the cell was obtained using the CCD detector attached microscopic objective lens For experiments with individual cells, this protocol allows correlations of the spatial locations of the Hz crystals in the parasite with the PTNB and of parameters of the PTNB with the parasite stage in each infected cell. For bulk ensemble cells experiments, this protocol also allows counting of MIRBCs and uninfected RBCs in each laser-exposed area. The operation of the motorized microscope stage, lasers, oscilloscope and the image detector was controlled by custom-made program modules assembled using the LabView 8 platform (National Instruments Corporation, Austin, TX).

Malaria parasite infection model. Suspensions of Hz were prepared by adding 5 mg Hz crystals (InvivoGen, #HMZ-33-04) into 1 mL of sterile phosphate buffered saline (pH 7.4). This suspension was sonicated for 5 minutes at room temperature to obtain a more homogenous dispersion of the crystals. The sample for studying individual Hz crystals was prepared by diluting of the stock suspension 1000-fold and then dispersing 5 μL of this working suspension on standard microscope slides and coverslips.

P. falciparum, strain 3D7, was obtained from RBC stabilates preserved in liquid nitrogen (the level of parasitemia during storage is ≥10%). Cultures were maintained on plates at 37° C. at 5% parasitemia in RPMI 1640 (#31800-022, Gibco-Life Technology, Rockville, MD) supplemented with 0.5% Albumax II (#11021-029, Gibco-Life Technology, Rockville, MD) under a 5% $O_2$/5% $CO_2$/90% $N_2$ atmosphere as previously described by Trager and Jensen. Prior to laser treatment, the level of parasitemia of an aliquot of stock culture was measured by light microscopy using Giemsa staining and SYBR green I (#S7563, Molecular Probes, Eugene, OR) fluorescence. Cells, approximately $2-5\times10^3$, were examined for determining the percentage of infected cell (defined as parasitemia). Both staining techniques were used also for analyzing the percentage of infected cells 24 hours after laser treatment and 48 hours after laser treatment (FIG. 7d). The level of parasitemia was adjusted prior to laser treatment in asynchronous culture. Ring, trophozoite and schizont stages of intraerythrocytic Plasmodium falciparum were included in the samples. For fluorescent imaging of the parasites, a solution of SYBR green I (diluted to 10× concentration in complete medium) was added to an aliquot of a stock culture, the suspension was mixed, and the sample placed in the dark for 5 minutes. Cells were washed twice with complete medium to remove unbound SYBR green I before imaging.

RBC concentrations were counted for each sample with a hemocytometer before treatment (0 hours), 24 hours after laser treatment, and 48 hours after laser treatment. Cell concentration was adjusted to $7\times10^5$ cells/mL for the experiments with individual cells, $1\times10^7$ cells/mL for static bulk exposure of cell mixtures and $3\times10^6$ cells/mL for the flow experiments. For the experiments with individual cells, RBC suspensions were placed on Ibidi 6-channel plates (μ-Slide VI 0.4, #80606, Ibidi, LLC., Verona, WI). For the static exposure of cell mixtures, 35 mm Petri dishes were used, and for the flow experiments, an Ibidi 1 mm flow cuvette (μ-Slide VI 0.1, #80666, Ibidi, LLC., Verona, WI) was used. Experiments with individual cells were repeated three times under identical conditions. Bulk laser scans of blood samples were also performed three to four times under identical conditions. Flow treatment of infected blood was repeated four times under identical conditions, but while using new stocks of cultured parasites.

Microscopy-based imaging and counts of the cells stained with the two methods were used to detect and quantify infection. First, Giemsa staining (FIG. 7-I and -II) was used as a standard approach to identify ring and schizont stages of malaria parasite development and to measure the level of parasitemia, that is, the ratio of the MIRBCs to the total number of cells. Second, fluorescent staining with SYBR green I (FIG. 7-III) was used as additional independent method to identify MIRBCs and specific stages of the parasite development. SYBR green I staining was also used to identify viable parasites. Since the SYBR green 1 dye does not absorb the excitation laser radiation (532 nm), the dye was used in the PTNB experiments for identifying infected cells before and after their exposure to the laser excitation pulses. We used a continuous 473 nm laser (RGBLase LLC, Fremont, CA) for excitation of the SYBR green I fluorescence. The spectral properties of this dye excluded absorption of the excitation laser pulse at 532 nm.

To improve the accuracy of the identification and counts of MIRBCs and the developmental stage of the parasites, we employed laser scanning confocal microscopy (LSM 710, Carl Zeiss Inc.), which enabled much higher quality bright field (FIG. 7-II) and fluorescent (FIG. 7-III) images as compared to standard microscopy imaging. Depending on the level of parasitemia, we collected 10 to 20 frames for the images of 2500-5000 cells and used the two staining methods (Giemsa- and SYBR green I) to identify uninfected cells (FIG. 7a) and MIRBCs in early ring (FIG. 7b) and mature schizont (FIG. 7c) stages. We observed good correlation between the SYBR green I- and Giemsa-based counts for all three groups of cells (FIG. 7d). This correlation validates our use of the SYBR green I fluorescent method for real time monitoring of individual cells before and after exposure to single excitation laser pulses (FIG. 8). We observed that the PTNB, generated by the excitation of Hz, lyses the MIRBC but its membrane was apparently not fully destroyed and appeared to envelope the destroyed parasite fragments within the original location several hours after the single pulse treatment (FIG. 8).

PTNB generation. The ability of Hz to generate transient PTNBs was explored with isolated Hz nanocrystals in water (FIG. 9a). Single excitation laser pulses of specific fluence (70 ps or 14 ns, 532 nm) were applied and the generation of PTNB was detected by three distinct methods (see FIG. 6). Time-resolved optical scattering images, optical scattering and acoustic traces all showed the transient PTNB of nanosecond duration around Hz nanocrystals in response to single laser excitation pulse (FIG. 9a). A bright flash is seen in the scattering image (FIG. 9a-III), the expansion and collapse of the PTNB is reported in the optical scattering trace (FIG. 9a-IV), and a pressure transient induces a specific acoustic trace (FIG. 9a-V). The duration of the optical trace reports the PTNB lifetime and is a metric of the PTNB maximal size. PTNB lifetime increased with the energy (fluence) of the laser pulse and also depended upon its duration (FIG. 10a). The longer 14 ns pulse showed much lower efficacy for the PTNB generation, likely due to diffusive thermal losses from nanocrystal during slower optical excitation. These results show that Hz nanocrystals efficiently convert the optical energy of a short laser pulse into a localized, tunable and transient PTNB.

We next cultured malaria parasites, *Plasmodium falciparum* (strain 3D7), in human blood and exposed individual MIRBCs to single laser pulses (70 ps or 14 ns, 532 nm). Generation of PTNBs in MIRBCs was monitored with the three independent signals described above (see FIG. 6). The presence and stage of the parasite in each cell were verified with the two independent microscopy methods (FIG. 7), Giemsa staining with bright field imaging (FIGS. 9c and 9c-I) and SYBR green I staining with fluorescent imaging (FIGS. 9b and 9c-II). Using laser fluences similar to those in the isolated Hz experiments (40 mJ/cm$^2$), we detected PTNB in individual MIRBCs at early ring stage (FIG. 9b-III, -IV and -V) and mature schizont stage (FIG. 9c-III, -IV and -V). In all MIRBCs the PTNB locations coincided with those of the parasite (FIGS. 9b and 9c-II and -III). Identical excitation of the ring and schizont parasite stages returned different signal responses: the lifetime of the PTNB in schizont MIRBCs was ten-fold higher than that in ring MIRBCs (FIGS. 9b-IV, 9c-IV, 10b). These stage-specific differences appear to be a consequence of larger and more abundant Hz crystals in schizont stage parasites (FIGS. 7b and 7c), which greatly facilitates PTNB generation. The lifetimes of PTNB increased with the fluence of laser pulse thus increasing the sensitivity of the detection of parasite (FIG. 10b). Like with isolated Hz nanocrystals, we observed much higher efficacy of the PTNB generation with a short, 70 ps pulse compared to a longer, 14 ns pulse. We also found a good correlation between the amplitude of the acoustic trace and the lifetime of the PTNB as measured by optical scattering trace (FIG. 10c). This correlation verifies feasibility of acoustic detection of parasites in opaque biological tissue (e.g., through the skin) that would normally compromise optical detection.

Unlike MIRBCs, which sustained visible damage after a single laser pulse (FIGS. 9b-VI and 9c-VI), irradiation of uninfected RBCs under the same conditions did not generate PTNBs detectable by any of the three methods (FIGS. 9d-III-9d-V). Even more importantly, no signs of laser-induced damage or significant heating of uninfected RBCs were observed (FIGS. 9d-IV, 9d-VI). The selective generation of PTNBs in only MIRBC results from the combination of: (1) the five- to seven-fold higher optical absorbance of Hz compared to that of hemoglobin in RBCs and (2) temporally and spatially localized heat release and evaporation of liquid due to the nano-size of the Hz nanocrystals and the short duration of the laser pulse (70 ps) which prevented thermal diffusive losses from the nanocrystal.

These experiments demonstrate that the generation of *Plasmodium falciparum*-specific PTNBs in individual MIRBCs is similar to the generation of PTNBs around isolated Hz nanocrystals in water and its efficacy is maximal with the picosecond excitation pulses. Hz is found only in blood stage of malaria parasite, therefore laser-induced PTNBs can act as malaria parasite-specific cellular agents even at early ring stages when the Hz crystals are only tens of nanometers in size and difficult to detect in single cells by other known methods.

PTNB generation and detection. The duration of each light scattering trace was measured to determine the PTNB lifetime as the metric of the maximal size of the vapor PTNB. We observed steady increases in the PTNB lifetime with increasing fluence of the laser pulse (FIG. 10a). Both the threshold for bubble production and its lifetime depended upon laser pulse duration. The shortest, 70 ps, pulse generated the largest PTNBs and required the minimal threshold fluence (about 10 mJ/cm$^2$) whereas the longer 14 ns pulse had a higher threshold (about 40 mJ/cm$^2$) and generated smaller PTNBs (FIG. 10a). This pulse duration effect is determined by the size of the optical absorber. Hz nanocrystals are between approximately 50-1000 nm in diameter and generate PTNB more efficiently with a 70 ps pulse rather than with the longer 14 ns pulse. The latter pulse may be too long to prevent thermal losses and de-localization of the photo-heating effect. Absorbance of the 17 ps pulse by a Hz nanocrystal results in rapid evaporation of its surrounding water layers resulting in localized and tunable generation of vapor PTNBs.

Identical excitation of the ring and schizont parasite stages returned different signal responses. At low fluence (28 mJ/cm$^2$) only schizont MIRBCs returned PTNB-type responses, whereas the ring MIRBCs did not generate PTNBs (FIG. 10b). At higher fluence (40 mJ/cm$^2$), the lifetimes of the PTNBs in schizont MIRBCs was ten-fold greater than those observed in ring MIRBCs (FIGS. 9b, 9c, and 10b).

We also studied how the maximal diameter of the PTNB, a parameter that determines diagnostic sensitivity and parasiticidal efficacy, depends upon optical excitation conditions. Using light scattering trace detection (FIG. 9-IV), we measured the probability of PTNB generation and its lifetime in individual cells as a function of laser pulse fluence and duration at different parasite stages (FIG. 10b). The probability of formation and the lifetime of PTNBs increased with fluence. For the mature schizont stage-infected cells, the PTNB lifetime was more than ten-fold higher than that for early ring stage-infected cells treated with identical fluence of the laser pulse (FIG. 10b). These stage-specific differences are likely a consequence of the larger and more abundant Hz crystals in schizont stage parasites (FIGS. 7b and 7c). Increases in size and density of the crystals will likely increase efficacy of PTNB generation. Increased pulse duration from 70 ps to 14 ns under identical laser pulse fluence dramatically reduced the probability and lifetimes of the PTNBs (FIG. 10b), likely due to increased thermal diffusive losses during the longer excitation pulse. Similar effects were observed when the longer pulse was used for excitation of isolated Hz nanocrystals (FIG. 10a). Thus, short picosecond pulses may be optimal for generating diagnostically reliable vapor PTNBs in MIRBCs. Finally, we compared the acoustic and optical traces of MIRBCs (FIG. 10c) and found a good correlation between the acoustic amplitude to the PTNB lifetime as measured by the light scattering signals. This result is important for non-invasive clinical applications. Acoustic detection of parasites can be used with opaque and scattering biological tissues that would normally compromise optical, light scattering detection.

These results collectively show that short laser pulses may generate localized PTNB by photothermally exciting Hz nanocrystals in MIRBCs without affecting uninfected RBCs. The maximal diameter of vapor PTNBs is estimated to be 0.5-1 µm for a 100 ns lifetime. This size is sufficient to readily measure optical light scattering (FIGS. 9b-III and -IV, 9c-III and -IV) and acoustic signals (FIG. 9b-V and 9c-V column V) due to pressure transients generated during the formation and collapse of the bubble. In addition, the localized explosive effect of PTNB formation is large enough to mechanically burst and destroy the parasite (FIGS. 9b-VI, 9c-VI, 13).

PTNB lifetime. Parameters of PTNB were analyzed through the PTNB lifetime (the metric of the maximal diameter of PTNB) as function of laser fluence, pulse duration, and number of laser pulses applied to the same Hz crystals. Dependencies of the PTNB lifetime upon fluence were obtained for two durations of the laser excitation pulse, 500 ps and 70 ps (FIG. 11a). We observed good tunability of the PTNB lifetime through the fluence: increase of laser fluence resulted in controllable increase of the lifetime of PTNB. At higher fluence, we observed higher efficacy of PTNB generation for the 500 ps pulse compared to the shorter 70 ps pulse. Based on our previous experience, we estimated that PTNBs with a lifetime above 150 nanoseconds kill the host cell, whereas smaller PTNBs can be generated without disrupting the RBC membrane. Therefore, laser pulse fluence can be used for controlling the therapeutic effect of Hz-generated PTNB. The stability of Hz crystals was studied under pulsed laser exposure, heating, and bubble generation for 500 ps pulses (FIG. 11b). The same Hz crystal was exposed to several identical pulses of relatively low fluence with a 5 second interval. We observed a rapid decrease of the PTNB lifetime that was caused by deterioration and destruction of the Hz crystal.

Diagnostic properties. The diagnostic properties of laser-induced PTNB were studied in mixtures of MIRBCs and uninfected RBCs with simultaneous scanning of cultures with broad-diameter single laser pulses (532 nm, 70 ps, diameter 210 µm) (FIG. 12a). The MIRBCs and their stage (ring or schizont) were identified and counted in each cell field prior to the laser exposure using SYBR green I-specific fluorescence (FIG. 12a, inset). We obtained acoustic traces for each laser-exposed field with an acoustic sensor located 2-3 mm from the cells. The ratio of MIRBCs to uninfected RBCs was varied by diluting the infected sample with normal blood. Fields lacking MIRBCs returned no signal (FIG. 12b, green trace), whereas fields with even a single, ring stage MIRBC returned PTNB-specific traces at MIRBC to RBC ratios of greater than or equal to 1 to $10^4$ (FIG. 12b, red trace). The acoustic traces detected for schizont stage MIRBCs had much higher amplitude (FIG. 12b, black trace). These differential signals could in principle allow diagnosis of the infection stage with single cell sensitivity. Due to the manual registration and analysis of the signals we limited our counts to between 30 and 40 fields (i.e., between 24 to 32000 cells) and, thus, did not study higher ratios of MIRBCs to RBCs. Nevertheless, these data support the feasibility of detection of MIRBCs with the sensitivity of 1 MIRBC for every $10^6$ RBC by automatic counting and analysis of acoustic traces of PTNB during trans-cutaneous delivery of laser pulses into blood vessels just under the skin by externally scanning optical fiber probe with acoustic sensor. This approach has the potential to provide highly sensitive, non-invasive and label- and needle-free in vivo detection of individual MIRBCs within several seconds.

Parasiticidal effects of PTNBs were analyzed by comparing the percentage of MIRBCs among all cells as a measure of parasitemia before and after bulk single pulse laser treatment of blood in a flow system (FIG. 16). The explosive mechanical action of the intra-parasite PTNB appears to immediately burst and destroy the parasites (FIGS. 9b, 9c VI; see also FIGS. 8 and 13). We applied 70 ps pulses at two fluence levels, 35 mJ/cm$^2$ and 130 mJ/cm$^2$, and 14 ns pulses of 70 mJ/cm$^2$ fluence that corresponded to 40-60 ns lifetimes of the PTNBs in MIRBCs as was found previously (see FIG. 10b). The flow rate, laser beam diameter and laser pulse repetition rate were synchronized to provide a single laser pulse exposure to each cell flown through the system. The level of parasitemia and the cell concentration were measured for 3000-4000 cells at three time-points: before treatment (0 hours), 24 hours after laser treatment, and 48 hours after laser treatment, using Giemsa bright field and SYBR green 1 fluorescent imaging (FIG. 12c). In addition to the bulk PTNB treatment, we applied a standard malaria drug, chloroquine, in a therapeutic dose of 1 µM[15]. The PTNB mode showed three-fold higher parasiticidal efficacy than chloroquine and rapidly reduced the level of MIRBCs to between 5% and 7% of that in the untreated sample at 24 hours (FIG. 12c). The concentration of uninfected RBCs did not show any detectable changes 24 hours or 48 hours after the 70 ps laser treatment. The maximal parasiticidal effect was observed for combinatorial treatment with PTNBs and drugs after 48 hours (FIG. 12c).

Destruction of malaria parasites. The immediate mechanical destruction caused by rapid expansion of the PTNB around Hz nanocrystals in the parasite food vacuole destroys the parasite but does not immediately cause loss of fluorescence of the SYBR green I dye. DNA, which will also cause SYBR green I fluorescence, is likely still present in the parasite fragments in the original location of the laser-treated cell. Therefore, to quantify remaining viability of infected cells after laser treatment, we quantified the number of the MIRBCs at 24 hours after treatment and 48 hours after treatment (levels of parasitemia). These time intervals are long enough to allow significant multiplication of any viable parasites as was observed for the untreated samples of MIRBCs (FIG. 12c). The lack of multiplication and, more importantly, the decrease in the level of MIRBCs after laser treatment (FIG. 12c) is most likely due to PTNB-induced lethality of parasites. Generation of PTNB in the MIRBCs under a high fluence of the excitation short laser pulse also often induced the lysis of the host cells (FIG. 13) due to mechanical perforation of the RBC membrane. However, even under these more destructive conditions, uninfected RBCs had no detectable damage (FIG. 13). This result confirms the localized, malaria parasite-specific nature of the Hz-derived PTNB whose mechanical impact was confined by the MIRBC.

It should be noted that increasing the fluence of the short 70 ps pulse beyond 40 $mJ/cm^2$ did not enhance the parasiticidal efficacy (FIG. 12c), and a longer 14 ns pulse showed lower parasiticidal efficacy (FIG. 12c) and, at the same time, lysed roughly 25% of the uninfected RBCs, due to more delocalized photothermal heating.

Destruction of malaria parasites: additional data. MIRBCs were modeled by mixing and incubating normal RBC with Hz crystals. Then RBCs containing Hz adsorbed to the cell membranes were mixed with normal RBC (FIG. 14a). All cells were treated with single identical laser pulses at the fluence that was previously determined to generate PTNBs around Hz crystals (532 nm, 400 ps, 31 $mJ/cm^2$). Generation of PTNBs was optically monitored through time-resolved optical scattering imaging and through time-responses of individual cells. Cells were imaged before laser treatment (FIG. 14a) and immediately after (FIG. 14b). We observed selective destruction (lysis) of MIRBC model cells (i.e., Hz adsorbed to the surface), while normal RBCs were not damaged. Such high selectivity of cell destruction correlated very well with the generation of PTNBs: they were observed only in MIRBC models (FIGS. 14c and 14d), whereas normal RBCs did not produce any PTNBs (FIG. 14c, 14e). Since the lifetime of Hz-generated PTNB was, as a rule, above 100 ns at the fluence applied, we concluded that MIRBC model cells were destructed with relatively large PTNBs (as shown in FIG. 2d).

PTNB and hyperthermia. Because Hz crystals were previously reported as the photothermal targets for laser-, radiofrequency- and magnetic-based hyperthermia treatments of malaria, we experimentally compared the efficacy and optical dose in PTNB generation and hyperthermia modes. The heating mode was achieved by using the same optical pulse of low fluence that caused localized transient heating of Hz crystals but without generation of PTNBs (FIG. 15). Laser pulses were applied at 10 hertz for 10 seconds and longer. The thermal effect was confirmed with optical responses (FIG. 15d) of specific shape that indicated fast heating and gradual cooling. Despite apparent heating of the target and increased optical dose (100 $mJ/cm^2$ against 31 $mJ/cm^2$ used in the PTNB mode) we did not observe any apparent damage to MIRBC model cells (adsorbed Hz) (FIGS. 15b and 15f), whereas the MIRBC models treated in PTNB mode were destroyed after a single laser pulse. This experiment demonstrated higher efficacy, shorter treatment time, and lower optical dose of the treatment in PTNB mode and a totally different mechanism than that of the hyperthermia mode.

Experimental set up for the bulk flow treatment of the blood We designed a closed sterile flow system (FIG. 16) that included an optically transparent flow cuvette (μ-Slide VI 0.1, #80666, Ibidi, LLC., Verona, WI) connected to two syringes, one dispensing and one collecting the RBC suspension. Both syringes were synchronously driven with computer-controlled pumps (NE-1000, New Era Pump Systems, Inc., Farmingdale, NY). The excitation laser beam was directed through the cuvette. The geometry of the channel (rectangular cross-section 1 mm wide, 0.1 mm deep and 15 mm length) ensures laminar flow with a two-dimensional monolayer of flowing cells being formed in the middle of the cuvette. The syringes were kept at physiological temperature by the automated heating sleeves. The diameter of the excitation laser beam was increased to 1.8 mm to provide uniform irradiation of all cells in the 1 mm by 1 mm area of the cuvette for each pulse. Flow rate was adjusted to the laser pulse repetition rate (10-40 hertz) to ensure single pulse exposure to each cell flowing through the cuvette. A low flow rate was used to treat 1 mL of the cell suspension in several minutes. The flow rate was limited in our experiments by the energy of the laser pulse and by the pulse repetition rate. Commercial lasers with 200-400 mJ/pulses and 100 hertz repetition rates will allow an increase in the treatment rate to 500 mL/min. This rate would allow the treatment of all the blood cells of a patient in 10 to 20 minutes.

We applied the following protocol for the flow treatment of the MIRBCs:

The initial level of parasitemia was calculated with the two methods as described above.

The cell suspension was adjusted to $3 \times 10^6$ cell/mL.

Cells were flown through the system and then exposed to a specific pulsed laser fluence.

Collected cells were cultured for another 48 hours.

Cell concentration and the levels of parasitemia were measured before treatment (0 hours), 24 hours after laser treatment, and 48 hours after laser treatment.

In the experiments that included the drug chloroquine, chloroquine (C6628, Sigma-Aldrich LLC, Saint Louis, MO) was added to the cell suspensions immediately prior to the flow treatment. A drug dose of 1 μM was calculated to match the therapeutic level used in most treatment regimens. Each treatment was repeated 3-4 times for different blood samples, each of which was cultured independently.

The parasiticidal effect of the bulk flow treatment was analyzed using the following parameters:

The absolute level of MIRBCs (parasitemia level) at 24 hours after laser treatment and 48 hours after treatment was measured and compared to that of the initial, untreated samples. This metric was used to estimate the efficacy of the specific treatment mode and to compare different treatments at one time-point.

The relative level of MIRBCs was calculated for each time point as the ratio of the absolute levels of MIRBCs in the treated sample to that in the untreated control with intact blood cells. This metric was used to compare the parasiticidal kinetics in the different non-synchronized samples of MIRBCs.

The total cell concentration characterized the safety of the treatment to uninfected cells. The concentration of RBCs was measured at each time point and was compared to the initial concentration of the cells in the suspension prior to flow treatment.

Devices for malaria diagnostics, therapeutics, and theranostics. Devices for the diagnosis and/or treatment of malaria may include devices similar to those described herein and may include an optically transparent cuvette that allows for blood containing MIRBC to be exposed to short laser pulses (FIG. 17a). Diagnostic and treatment devices may be similar to the prototype we constructed, which included a transparent flow cuvette and a syringe pump that flows the cell suspension through the cuvette (FIG. 17b). Devices appropriate for in vivo diagnosis and/or treatment may include at least an optical fiber probe, a photodetector, an ultrasound detector, and a computer, or some combination of these components (FIG. 18a). Devices appropriate for in vivo applications may allow excitation laser radiation to be directed with a fiber probe into a sub-cutaneous blood vessel or vessels where PTNBs may be generated in MIRBCs (FIG. 18b). Certain devices may be similar to the prototype we constructed that include a fiber system for PTNB generation and detection (FIG. 18c).

The experiments described above demonstrate selective generation of PTNB around Hz crystals, the ability to guide and detect PTNB generation in real time with three different techniques, the therapeutic feasibility of the method for destroying infected RBCs, the high therapeutic selectivity of the method which prevents destruction of uninfected cells, and the possibility combining the diagnosis (based on PTNB detection), guidance of treatment (with PTNB of specific lifetime) and destruction of parasites and/or MIRBCs (based on the parameters of PTNB signals) in one theranostic procedure.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A system comprising:
   a tunable pulsed laser;
   an optical fiber probe configured to deliver a laser pulse from the tunable pulsed laser, wherein the optical fiber probe is further configured to receive optical scattering signals, wherein the laser pulse comprises a pulse duration of 70 picoseconds to about 14 nanoseconds, a wavelength of from about 400 nanometers to about 1200 nanometers, and a pulse fluence from about 20 $mJ/cm^2$ to about 250 $mJ/cm^2$;
   an optical detector for detecting said optical scattering signals;
   a computer operatively connected to the optical detector to process the optical signals received therefrom, wherein the computer is further operatively connected to the tunable pulsed laser; and
   wherein the computer is configured to control pulse duration, wavelength, and pulse fluence of the tunable pulsed laser; and
   wherein the computer is configured to determine the presence of at least one hemozoin nanocrystal based on the optical signals received from the optical detector following a laser pulse from the tunable pulsed laser by generating a time-resolved optical scattering image, wherein the at least one hemozoin nanocrystal is present if the time-resolved optical scattering image depicts a change in photodetector signal of at least 0.10 V for at least 10 ns.

2. The system of claim 1, wherein the wavelength is from about 640 nanometers to about 660 nanometers.

3. The system of claim 1, wherein the wavelength is 532 nanometers.

4. The system of claim 1, wherein the pulse fluence is from about 25 $mJ/cm^2$ to about 40 $mJ/cm^2$.

5. The system of claim 1, further comprising an ultrasound detector for detecting an acoustic signal, wherein the computer is operatively connected to the ultrasound detector to process the acoustic signal received therefrom, and wherein the computer is further configured to determine the presence of the at least one hemozoin nanocrystal by identifying the acoustic signal received from the ultrasound detector as a pressure pulse emitted from the at least one hemozoin nanocrystal, wherein the pressure pulse emitted from the at least one hemozoin nanocrystal comprises a pulse of at least 0.01 V.

6. The system of claim 1, wherein the computer is configured to determine the presence of the malaria-specific nanoparticle in the red blood cells as the laser pulse excites the red blood cells by generating an optical scattering time response sufficient to measure the maximal diameter and lifetime of the photothermal nanobubble.

* * * * *